United States Patent
Frazier et al.

(10) Patent No.: US 12,336,750 B2
(45) Date of Patent: Jun. 24, 2025

(54) SOFT PALATE TREATMENT

(71) Applicant: Aerin Medical Inc., Sunnyvale, CA (US)

(72) Inventors: Andrew Frazier, Sunnyvale, CA (US); Scott J. Wolf, Menlo Park, CA (US); Fred Dinger, Sunnyvale, CA (US); Charlton Yih, San Mateo, CA (US)

(73) Assignee: Aerin Medical Inc., Mountain View, CA (US)

( * ) Notice: Subject to any disclaimer, the term of this patent is extended or adjusted under 35 U.S.C. 154(b) by 0 days.

(21) Appl. No.: 18/474,971

(22) Filed: Sep. 26, 2023

(65) Prior Publication Data

US 2024/0122641 A1   Apr. 18, 2024

Related U.S. Application Data

(63) Continuation of application No. 15/930,676, filed on May 13, 2020, now Pat. No. 11,806,071, which is a
(Continued)

(51) Int. Cl.
*A61B 18/14*   (2006.01)
*A61B 18/02*   (2006.01)
(Continued)

(52) U.S. Cl.
CPC .......... *A61B 18/1485* (2013.01); *A61B 18/02* (2013.01); *A61B 18/082* (2013.01);
(Continued)

(58) Field of Classification Search
CPC .............. A61B 18/1485; A61B 18/082; A61B 18/1442; A61B 2018/1467;
(Continued)

(56) References Cited

U.S. PATENT DOCUMENTS

| 874,178 A | 12/1907 | DeForest |
| 3,117,571 A | 1/1964 | Fry et al. |

(Continued)

FOREIGN PATENT DOCUMENTS

| CN | 2225227 Y | 4/1996 |
| CN | 2621723 | 6/2004 |

(Continued)

OTHER PUBLICATIONS

"Electrosurgery Console", U.S. Appl. No. 29/668,608, filed Oct. 31, 2018, 12 pages.
(Continued)

*Primary Examiner* — Thomas A Giuliani
(74) *Attorney, Agent, or Firm* — Greenberg Traurig, LLP; David J. Dykeman; Roman Fayerberg

(57) ABSTRACT

A method of treating a soft palate in a patient may involve advancing a tissue treatment portion of a soft palate treatment device through the patient's mouth, contacting a treatment surface of the tissue treatment portion with mucosal tissue of the soft palate, and delivering energy from the tissue treatment portion through the mucosal tissue to a target tissue in the soft palate beneath to the mucosal tissue, to change at least one property of the target tissue. The method may further involve cooling the mucosal tissue with a cooling member on the treatment surface of the tissue treatment portion and removing the tissue treatment portion from the mouth.

14 Claims, 18 Drawing Sheets

Related U.S. Application Data continuation-in-part of application No. 15/848,951, filed on Dec. 20, 2017, now Pat. No. 11,116,566.

(60) Provisional application No. 62/847,438, filed on May 14, 2019, provisional application No. 62/438,300, filed on Dec. 22, 2016.

(51) Int. Cl.
| | |
|---|---|
| *A61B 18/08* | (2006.01) |
| *A61B 18/18* | (2006.01) |
| *A61B 17/32* | (2006.01) |
| *A61B 18/00* | (2006.01) |
| *A61B 18/12* | (2006.01) |

(52) U.S. Cl.
CPC .......... *A61B 18/1815* (2013.01); *A61B 2017/320069* (2017.08); *A61B 2018/00023* (2013.01); *A61B 2018/00577* (2013.01); *A61B 2018/00821* (2013.01); *A61B 2018/1253* (2013.01); *A61B 2018/126* (2013.01); *A61B 2018/1422* (2013.01); *A61B 2218/007* (2013.01)

(58) Field of Classification Search
CPC .... A61B 2018/143; A61B 2018/00815; A61B 2018/00023; A61B 2018/00577; A61B 2018/00821; A61B 2018/126; A61B 2018/1422; A61B 2018/00005; A61B 2018/00011; A61B 2018/00017; A61B 2018/0016; A61B 2018/00327; A61B 2018/1465; A61B 2018/00642; A61B 2018/00797; A61B 2017/320069; A61B 2017/248; A61B 2218/007
USPC ........ 606/27, 28, 41, 42, 45–52; 607/98, 99, 607/101, 102, 104, 105, 107, 113, 115, 607/116
See application file for complete search history.

(56) References Cited

U.S. PATENT DOCUMENTS

| | | |
|---|---|---|
| 3,538,919 A | 11/1970 | Meyer |
| 3,941,121 A | 3/1976 | Olinger et al. |
| 4,074,718 A | 2/1978 | Morrison |
| 4,271,848 A | 6/1981 | Turner et al. |
| 4,411,266 A | 10/1983 | Cosman |
| 4,887,605 A | 12/1989 | Angelsen et al. |
| 5,255,679 A | 10/1993 | Imran |
| 5,348,008 A | 9/1994 | Bornn et al. |
| 5,505,730 A | 4/1996 | Edwards |
| 5,507,725 A | 4/1996 | Savage et al. |
| 5,514,131 A * | 5/1996 | Edwards ............... A61N 1/403 606/41 |
| 5,533,499 A | 7/1996 | Johnson |
| 5,542,916 A | 8/1996 | Hirsch et al. |
| 5,562,720 A | 10/1996 | Stern et al. |
| 5,575,788 A | 11/1996 | Baker et al. |
| 5,611,798 A | 3/1997 | Eggers |
| 5,624,439 A | 4/1997 | Edwards et al. |
| 5,674,191 A | 10/1997 | Edwards et al. |
| 5,697,536 A | 12/1997 | Eggers et al. |
| 5,707,349 A | 1/1998 | Edwards |
| 5,718,702 A | 2/1998 | Edwards |
| 5,728,094 A | 3/1998 | Edwards |
| 5,730,719 A | 3/1998 | Edwards |
| 5,733,280 A | 3/1998 | Avitall |
| 5,738,114 A | 4/1998 | Edwards |
| 5,743,870 A | 4/1998 | Edwards |
| 5,743,904 A | 4/1998 | Edwards |
| 5,746,224 A | 5/1998 | Edwards |
| 5,766,153 A | 6/1998 | Eggers et al. |
| 5,766,605 A | 6/1998 | Sanders et al. |
| 5,800,429 A | 9/1998 | Edwards |
| 5,807,306 A | 9/1998 | Shapland et al. |
| 5,816,095 A | 10/1998 | Nordell, II et al. |
| 5,817,049 A | 10/1998 | Edwards |
| 5,820,580 A | 10/1998 | Edwards et al. |
| 5,823,197 A | 10/1998 | Edwards |
| 5,827,277 A | 10/1998 | Edwards |
| 5,843,021 A | 12/1998 | Edwards et al. |
| 5,843,077 A | 12/1998 | Edwards |
| 5,846,235 A | 12/1998 | Pasricha et al. |
| 5,879,349 A | 3/1999 | Edwards |
| 5,891,134 A | 4/1999 | Goble et al. |
| 5,938,659 A | 8/1999 | Tu et al. |
| 5,944,715 A | 8/1999 | Goble |
| 6,026,816 A | 2/2000 | McMillan et al. |
| 6,033,397 A | 3/2000 | Laufer et al. |
| 6,045,549 A | 4/2000 | Smethers et al. |
| 6,096,033 A | 8/2000 | Tu et al. |
| 6,102,907 A | 8/2000 | Smethers et al. |
| 6,106,520 A | 8/2000 | Laufer et al. |
| 6,109,268 A | 8/2000 | Thapliyal et al. |
| 6,126,657 A | 10/2000 | Edwards et al. |
| 6,131,579 A | 10/2000 | Thorson et al. |
| 6,139,546 A | 10/2000 | Koenig et al. |
| 6,152,143 A | 11/2000 | Edwards |
| 6,165,173 A | 12/2000 | Kamdar et al. |
| 6,179,803 B1 | 1/2001 | Edwards et al. |
| 6,210,355 B1 | 4/2001 | Edwards et al. |
| 6,228,079 B1 | 5/2001 | Koenig |
| 6,231,569 B1 | 5/2001 | Bek et al. |
| 6,238,394 B1 | 5/2001 | Garito et al. |
| 6,273,886 B1 | 8/2001 | Edwards et al. |
| 6,273,907 B1 | 8/2001 | Laufer |
| 6,293,941 B1 | 9/2001 | Strul et al. |
| 6,309,386 B1 | 10/2001 | Bek |
| 6,371,926 B1 | 4/2002 | Thorson et al. |
| 6,383,181 B1 | 5/2002 | Johnston et al. |
| 6,391,028 B1 | 5/2002 | Fanton et al. |
| 6,405,732 B1 | 6/2002 | Edwards et al. |
| 6,416,491 B1 | 7/2002 | Edwards et al. |
| 6,416,505 B1 | 7/2002 | Fleishman et al. |
| 6,425,151 B2 | 7/2002 | Barnett |
| 6,431,174 B1 | 8/2002 | Knudson et al. |
| 6,451,013 B1 | 9/2002 | Bays et al. |
| 6,502,574 B2 | 1/2003 | Stevens et al. |
| 6,517,534 B1 | 2/2003 | McGovern et al. |
| 6,517,535 B2 | 2/2003 | Edwards |
| 6,530,924 B1 * | 3/2003 | Ellman ............... A61B 18/149 606/49 |
| 6,551,310 B1 | 4/2003 | Ganz et al. |
| 6,562,036 B1 | 5/2003 | Ellman et al. |
| 6,575,969 B1 | 6/2003 | Rittman et al. |
| 6,589,235 B2 | 7/2003 | Wong et al. |
| 6,640,120 B1 | 10/2003 | Swanson et al. |
| 6,658,279 B2 | 12/2003 | Swanson et al. |
| 6,659,106 B1 | 12/2003 | Hovda et al. |
| 6,669,689 B2 | 12/2003 | Lehmann et al. |
| 6,685,648 B2 | 2/2004 | Flaherty et al. |
| 6,896,674 B1 | 5/2005 | Woloszko et al. |
| 6,911,027 B1 | 6/2005 | Edwards et al. |
| 6,978,781 B1 | 12/2005 | Jordan |
| 7,055,523 B1 | 6/2006 | Brown |
| 7,097,641 B1 | 8/2006 | Arless et al. |
| 7,114,495 B2 | 10/2006 | Lockwood, Jr. |
| 7,322,993 B2 | 1/2008 | Metzger et al. |
| 7,361,168 B2 | 4/2008 | Makower et al. |
| 7,416,550 B2 | 8/2008 | Protsenko et al. |
| 7,442,191 B2 | 10/2008 | Hovda et al. |
| 7,572,251 B1 | 8/2009 | Davison et al. |
| 7,628,789 B2 | 12/2009 | Soltesz et al. |
| 7,655,243 B2 | 2/2010 | Deem et al. |
| 7,678,069 B1 | 3/2010 | Baker et al. |
| 7,780,730 B2 | 8/2010 | Saidi |
| 7,824,394 B2 | 11/2010 | Manstein |
| 7,850,683 B2 | 12/2010 | Elkins et al. |
| 7,997,278 B2 | 8/2011 | Utley et al. |
| 8,088,122 B2 | 1/2012 | Li et al. |
| 8,114,062 B2 | 2/2012 | Muni et al. |

(56) References Cited

U.S. PATENT DOCUMENTS

| | | |
|---|---|---|
| 8,128,617 B2 | 3/2012 | Bencini et al. |
| 8,137,345 B2 | 3/2012 | McNall, III et al. |
| 8,317,781 B2 | 11/2012 | Owens et al. |
| 8,317,782 B1 | 11/2012 | Ellman et al. |
| 8,718,786 B2 | 5/2014 | Shalev |
| D716,325 S | 10/2014 | Brudnicki |
| 8,925,551 B2 | 1/2015 | Sanders |
| 8,936,594 B2 | 1/2015 | Wolf et al. |
| 8,939,970 B2 | 1/2015 | Stone et al. |
| 8,979,841 B2 | 3/2015 | Kunis et al. |
| 8,986,301 B2 | 3/2015 | Wolf et al. |
| 9,072,597 B2 | 7/2015 | Wolf et al. |
| 9,119,954 B2 | 9/2015 | Burdette et al. |
| 9,125,677 B2 | 9/2015 | Sobol et al. |
| 9,179,964 B2 | 11/2015 | Wolf et al. |
| 9,179,967 B2 | 11/2015 | Wolf et al. |
| 9,237,924 B2 | 1/2016 | Wolf et al. |
| 9,247,989 B2 | 2/2016 | Truckai |
| D763,910 S | 8/2016 | Drozd |
| D765,091 S | 8/2016 | Del Lima |
| 9,415,194 B2 | 8/2016 | Wolf et al. |
| D765,718 S | 9/2016 | Vinna |
| 9,433,463 B2 | 9/2016 | Wolf et al. |
| 9,452,010 B2 | 9/2016 | Wolf et al. |
| 9,452,087 B2 | 9/2016 | Holm et al. |
| 9,486,278 B2 | 11/2016 | Wolf et al. |
| 9,498,241 B2 * | 11/2016 | Leonhard ............... A61B 17/29 |
| 9,526,571 B2 | 12/2016 | Wolf et al. |
| 9,526,652 B2 | 12/2016 | Harrison et al. |
| D776,717 S | 1/2017 | Asai |
| D782,657 S | 3/2017 | Williams |
| D789,383 S | 6/2017 | Bawazeer |
| 9,687,288 B2 | 6/2017 | Saadat |
| 9,687,296 B2 | 6/2017 | Wolf et al. |
| D795,898 S | 8/2017 | Li |
| D797,756 S | 9/2017 | Meyer |
| 9,763,723 B2 | 9/2017 | Saadat |
| 9,763,743 B2 | 9/2017 | Lin et al. |
| 9,770,293 B2 | 9/2017 | Dresher |
| 9,788,886 B2 | 10/2017 | Wolf et al. |
| 9,801,752 B2 | 10/2017 | Wolf et al. |
| 9,888,957 B2 | 2/2018 | Wolf et al. |
| 9,913,682 B2 | 3/2018 | Wolf et al. |
| 9,943,361 B2 | 4/2018 | Wolf et al. |
| 10,028,780 B2 | 7/2018 | Wolf et al. |
| 10,028,781 B2 | 7/2018 | Saadat |
| D840,428 S | 2/2019 | Narinedhat |
| D844,013 S | 3/2019 | Peeters |
| 10,265,115 B2 | 4/2019 | Wolf et al. |
| 10,307,200 B2 | 6/2019 | Saadat |
| 10,335,221 B2 | 7/2019 | Wolf et al. |
| D857,034 S | 8/2019 | Hung |
| 10,376,300 B2 | 8/2019 | Wolf et al. |
| D860,315 S | 9/2019 | Chen |
| 10,398,489 B2 | 9/2019 | Wolf et al. |
| 10,456,185 B2 | 10/2019 | Wolf et al. |
| 10,456,186 B1 | 10/2019 | Wolf et al. |
| 10,470,814 B2 | 11/2019 | Wolf et al. |
| 10,485,603 B2 | 11/2019 | Wolf et al. |
| D874,492 S | 2/2020 | Henderson |
| D875,742 S | 2/2020 | Kang |
| D877,171 S | 3/2020 | Poindexter |
| 10,603,059 B2 | 3/2020 | Dinger et al. |
| D880,694 S | 4/2020 | Ng et al. |
| D881,904 S | 4/2020 | Angeles et al. |
| 10,631,925 B2 | 4/2020 | Wolf et al. |
| 10,722,282 B2 | 7/2020 | Wolf et al. |
| D897,185 S | 9/2020 | Perkins, Jr. et al. |
| D897,186 S | 9/2020 | Perkins, Jr. et al. |
| 10,779,873 B2 | 9/2020 | Wolf et al. |
| D902,412 S | 11/2020 | Angeles et al. |
| D904,698 S | 12/2020 | Moeller et al. |
| D904,852 S | 12/2020 | Levand et al. |
| 10,864,035 B2 | 12/2020 | Hester et al. |
| D906,782 S | 1/2021 | Brinson et al. |
| D910,408 S | 2/2021 | Lin |
| D911,140 S | 2/2021 | Hyma et al. |
| D911,141 S | 2/2021 | Panosian et al. |
| 10,932,853 B2 | 3/2021 | Wolf et al. |
| 11,033,318 B2 | 6/2021 | Wolf et al. |
| D927,687 S | 8/2021 | Stoklund et al. |
| 11,116,566 B2 | 9/2021 | Dinger et al. |
| 11,241,271 B2 | 2/2022 | Wolf et al. |
| 11,304,746 B2 | 4/2022 | Wolf et al. |
| 11,457,971 B2 | 10/2022 | Wolf et al. |
| 11,759,222 B2 | 9/2023 | Wolf et al. |
| 11,766,286 B2 | 9/2023 | Wolf et al. |
| 11,801,084 B2 | 10/2023 | Wolf et al. |
| 11,806,071 B2 | 11/2023 | Frazier et al. |
| 11,832,876 B2 | 12/2023 | Wolf et al. |
| 11,883,091 B2 | 1/2024 | Townley |
| 11,896,818 B2 | 2/2024 | Townley |
| 11,969,200 B2 | 4/2024 | Hester et al. |
| 12,053,227 B2 | 8/2024 | Wolf et al. |
| 12,082,872 B2 | 9/2024 | Townley et al. |
| 2002/0010460 A1 | 1/2002 | Joye et al. |
| 2002/0016588 A1 | 2/2002 | Wong et al. |
| 2002/0035361 A1 | 3/2002 | Houser |
| 2002/0049464 A1 | 4/2002 | Donofrio et al. |
| 2002/0087155 A1 | 7/2002 | Underwood et al. |
| 2002/0120259 A1 | 8/2002 | Lettice et al. |
| 2002/0128641 A1 | 9/2002 | Underwood et al. |
| 2003/0069620 A1 | 4/2003 | Li |
| 2003/0139789 A1 | 7/2003 | Tvinnereim et al. |
| 2003/0144659 A1 | 7/2003 | Edwards |
| 2003/0208194 A1 | 11/2003 | Hovda et al. |
| 2003/0208250 A1 | 11/2003 | Edwards et al. |
| 2003/0225403 A1 | 12/2003 | Woloszko et al. |
| 2004/0030334 A1 | 2/2004 | Quick et al. |
| 2004/0193238 A1 | 9/2004 | Mosher et al. |
| 2004/0210214 A1 | 10/2004 | Knowlton |
| 2004/0215235 A1 | 10/2004 | Jackson et al. |
| 2004/0220644 A1 | 11/2004 | Shalev et al. |
| 2004/0230188 A1 | 11/2004 | Cioanta et al. |
| 2005/0020901 A1 | 1/2005 | Belson et al. |
| 2005/0119643 A1 | 6/2005 | Sobol et al. |
| 2005/0171522 A1 | 8/2005 | Christopherson |
| 2005/0171574 A1 | 8/2005 | Rubinsky et al. |
| 2005/0222565 A1 | 10/2005 | Manstein |
| 2005/0234439 A1 | 10/2005 | Underwood |
| 2005/0234443 A1 | 10/2005 | Rioux et al. |
| 2005/0240147 A1 | 10/2005 | Makower et al. |
| 2005/0288655 A1 | 12/2005 | Root et al. |
| 2005/0288665 A1 | 12/2005 | Woloszko |
| 2006/0004323 A1 | 1/2006 | Chang et al. |
| 2006/0009758 A1 | 1/2006 | Edwards et al. |
| 2006/0064086 A1 | 3/2006 | Odom |
| 2006/0095066 A1 | 5/2006 | Chang et al. |
| 2006/0190022 A1 | 8/2006 | Beyar et al. |
| 2006/0195169 A1 | 8/2006 | Gross et al. |
| 2006/0235377 A1 | 10/2006 | Earley et al. |
| 2006/0253117 A1 | 11/2006 | Hovda et al. |
| 2006/0265031 A1 | 11/2006 | Skwarek et al. |
| 2006/0276817 A1 | 12/2006 | Vassallo et al. |
| 2006/0276861 A1 | 12/2006 | Lin |
| 2007/0043350 A1 | 2/2007 | Soltesz et al. |
| 2007/0049999 A1 | 3/2007 | Esch et al. |
| 2007/0066944 A1 | 3/2007 | Nyte |
| 2007/0073282 A1 | 3/2007 | McGarrigan et al. |
| 2007/0083193 A1 | 4/2007 | Werneth et al. |
| 2007/0093710 A1 | 4/2007 | Maschke |
| 2007/0179495 A1 | 8/2007 | Mitchell et al. |
| 2007/0219600 A1 | 9/2007 | Gertner et al. |
| 2007/0244529 A1 | 10/2007 | Choi et al. |
| 2007/0287994 A1 | 12/2007 | Patel |
| 2008/0000477 A1 | 1/2008 | Huster et al. |
| 2008/0004613 A1 | 1/2008 | Barbut et al. |
| 2008/0021369 A1 | 1/2008 | Deem et al. |
| 2008/0027423 A1 | 1/2008 | Choi et al. |
| 2008/0027480 A1 | 1/2008 | van der Burg et al. |
| 2008/0027520 A1 | 1/2008 | Choi et al. |
| 2008/0082090 A1 | 4/2008 | Manstein |
| 2008/0125626 A1 | 5/2008 | Chang et al. |
| 2008/0154237 A1 | 6/2008 | Chang et al. |

(56) References Cited

U.S. PATENT DOCUMENTS

| | | |
|---|---|---|
| 2008/0154343 A1 | 6/2008 | Li et al. |
| 2008/0183251 A1 | 7/2008 | Azar et al. |
| 2008/0255642 A1 | 10/2008 | Zarins et al. |
| 2008/0312644 A1 | 12/2008 | Fourkas et al. |
| 2009/0018485 A1 | 1/2009 | Krespi et al. |
| 2009/0124958 A1 | 5/2009 | Li et al. |
| 2009/0143821 A1 | 6/2009 | Stupak |
| 2009/0163890 A1 | 6/2009 | Clifford et al. |
| 2009/0192505 A1 | 7/2009 | Askew et al. |
| 2009/0292358 A1 | 11/2009 | Saidi |
| 2009/0299355 A1 | 12/2009 | Bencini et al. |
| 2010/0049188 A1 | 2/2010 | Nelson et al. |
| 2010/0144996 A1 | 6/2010 | Kennedy et al. |
| 2010/0152730 A1 | 6/2010 | Makower et al. |
| 2010/0160906 A1 | 6/2010 | Jarrard |
| 2010/0174283 A1 | 7/2010 | McNall, III et al. |
| 2010/0204560 A1 | 8/2010 | Salahieh et al. |
| 2010/0241112 A1 | 9/2010 | Watson |
| 2010/0260703 A1 | 10/2010 | Yankelson et al. |
| 2010/0262133 A1 | 10/2010 | Hoey et al. |
| 2011/0009737 A1 | 1/2011 | Manstein |
| 2011/0118726 A1 | 5/2011 | De La Rama et al. |
| 2011/0125149 A1 | 5/2011 | El-Galley et al. |
| 2011/0130689 A1 | 6/2011 | Cohen et al. |
| 2011/0180064 A1 | 7/2011 | Tanaka et al. |
| 2011/0282268 A1 | 11/2011 | Baker et al. |
| 2011/0288477 A1 | 11/2011 | Ressemann et al. |
| 2011/0301587 A1 | 12/2011 | Deem et al. |
| 2012/0029512 A1 | 2/2012 | Willard et al. |
| 2012/0039954 A1 | 2/2012 | Cupit et al. |
| 2012/0059255 A1 | 3/2012 | Paul et al. |
| 2012/0078377 A1 | 3/2012 | Gonzales et al. |
| 2012/0123411 A1 | 5/2012 | Ibrahim et al. |
| 2012/0179154 A1 | 7/2012 | Goldberg et al. |
| 2012/0197361 A1 | 8/2012 | Gonzales et al. |
| 2012/0209257 A1 | 8/2012 | Van Der Weide et al. |
| 2012/0265188 A1 | 10/2012 | Buchbinder et al. |
| 2012/0271294 A1 | 10/2012 | Barthe et al. |
| 2012/0298105 A1 | 11/2012 | Osorio |
| 2012/0310233 A1 | 12/2012 | Dimmer et al. |
| 2012/0316473 A1 | 12/2012 | Bonutti et al. |
| 2012/0316557 A1 | 12/2012 | Sartor et al. |
| 2012/0323227 A1 | 12/2012 | Wolf et al. |
| 2012/0323232 A1 | 12/2012 | Wolf et al. |
| 2013/0085546 A1 | 4/2013 | Bolea et al. |
| 2013/0116679 A1 | 5/2013 | Van der Weide et al. |
| 2013/0158536 A1 | 6/2013 | Bloom |
| 2013/0165990 A1 | 6/2013 | Mathur et al. |
| 2013/0218158 A1 | 8/2013 | Danek et al. |
| 2013/0281997 A1 | 10/2013 | Davie |
| 2014/0088463 A1* | 3/2014 | Wolf ............... A61B 18/1477 606/199 |
| 2014/0114233 A1 | 4/2014 | Deem et al. |
| 2014/0243793 A1 | 8/2014 | Morriss et al. |
| 2014/0316396 A1 | 10/2014 | Wolf et al. |
| 2015/0141982 A1 | 5/2015 | Lee |
| 2015/0148791 A1 | 5/2015 | Birdsall et al. |
| 2015/0164571 A1* | 6/2015 | Saadat ............... A61B 17/24 600/109 |
| 2015/0202003 A1 | 7/2015 | Wolf et al. |
| 2016/0045277 A1 | 2/2016 | Lin et al. |
| 2016/0058336 A1 | 3/2016 | Blahnik et al. |
| 2016/0121112 A1 | 5/2016 | Azar |
| 2016/0274661 A1 | 9/2016 | Maeda |
| 2016/0287315 A1 | 10/2016 | Wolf et al. |
| 2016/0317803 A1 | 11/2016 | Sama |
| 2016/0331459 A1 | 11/2016 | Townley |
| 2016/0354136 A1 | 12/2016 | Saadat |
| 2017/0105793 A1 | 4/2017 | Cao |
| 2017/0224987 A1 | 8/2017 | Kent et al. |
| 2017/0231651 A1 | 8/2017 | Dinger et al. |
| 2017/0252089 A1 | 9/2017 | Hester |
| 2017/0252100 A1 | 9/2017 | Wolf et al. |
| 2017/0357419 A1 | 12/2017 | Raymann |
| 2017/0360495 A1 | 12/2017 | Wolf et al. |
| 2018/0000535 A1 | 1/2018 | Wolf et al. |
| 2018/0103940 A1 | 4/2018 | Shin et al. |
| 2018/0177542 A1 | 6/2018 | Wolf et al. |
| 2018/0177546 A1 | 6/2018 | Dinger et al. |
| 2018/0185085 A1 | 7/2018 | Wolf et al. |
| 2018/0228533 A1 | 8/2018 | Wolf et al. |
| 2018/0228551 A1 | 8/2018 | Moe |
| 2018/0263678 A1 | 9/2018 | Saadat |
| 2018/0317997 A1 | 11/2018 | Dinger et al. |
| 2018/0333195 A1 | 11/2018 | Greep et al. |
| 2018/0344378 A1 | 12/2018 | Wolf et al. |
| 2019/0076185 A1 | 3/2019 | Dinger et al. |
| 2019/0151005 A1 | 5/2019 | Wolf et al. |
| 2019/0175242 A1 | 6/2019 | Wolf et al. |
| 2019/0201069 A1 | 7/2019 | Wolf et al. |
| 2019/0231409 A1 | 8/2019 | Wolf et al. |
| 2019/0282289 A1 | 9/2019 | Wolf et al. |
| 2019/0290352 A1 | 9/2019 | Viswanadha et al. |
| 2019/0336196 A1 | 11/2019 | Wolf et al. |
| 2019/0343577 A1 | 11/2019 | Wolf et al. |
| 2019/0357927 A1 | 11/2019 | Palushi |
| 2020/0100829 A1 | 4/2020 | Wolf et al. |
| 2020/0129223 A1 | 4/2020 | Angeles et al. |
| 2020/0170699 A1 | 6/2020 | Wolf et al. |
| 2020/0205884 A1 | 7/2020 | Wolf et al. |
| 2020/0268439 A1 | 8/2020 | Frazier et al. |
| 2020/0375648 A1 | 12/2020 | Wolf et al. |
| 2020/0405383 A1 | 12/2020 | Townley |
| 2021/0169566 A1 | 6/2021 | Townley |
| 2021/0275241 A1 | 9/2021 | Fahey |
| 2021/0315638 A1 | 10/2021 | Townley et al. |
| 2022/0071802 A1 | 3/2022 | Christopherson |
| 2022/0142699 A1 | 5/2022 | Wolf et al. |
| 2022/0151689 A1 | 5/2022 | Yih et al. |
| 2022/0257272 A1 | 8/2022 | Wolf et al. |
| 2022/0361941 A1 | 11/2022 | Townley |
| 2023/0062359 A1 | 3/2023 | Wolf et al. |
| 2023/0293222 A1 | 9/2023 | Wolf et al. |
| 2024/0024016 A1 | 1/2024 | Wolf et al. |
| 2024/0050143 A1 | 2/2024 | Wolf et al. |
| 2024/0050148 A1 | 2/2024 | Wolf et al. |
| 2024/0315755 A1 | 9/2024 | Wolf et al. |
| 2024/0366286 A1 | 11/2024 | Wolf et al. |

FOREIGN PATENT DOCUMENTS

| | | |
|---|---|---|
| CN | 101325919 | 12/2008 |
| CN | 101883606 | 11/2010 |
| CN | 103055417 | 4/2013 |
| DE | 102007006467 | 3/2008 |
| WO | 1999007299 | 2/1999 |
| WO | 1999030655 A1 | 6/1999 |
| WO | 2001043653 | 6/2001 |
| WO | 2003024349 | 3/2003 |
| WO | 2007037895 | 4/2007 |
| WO | 2007134005 | 11/2007 |
| WO | 2009048580 | 4/2009 |
| WO | 2010077980 | 7/2010 |
| WO | 2010077980 A1 | 7/2010 |
| WO | 2012174161 | 12/2012 |
| WO | 2013028998 A2 | 2/2013 |
| WO | 2015047863 | 4/2015 |
| WO | 2015048806 | 4/2015 |
| WO | 2015153696 | 10/2015 |
| WO | 2016183337 A2 | 11/2016 |

OTHER PUBLICATIONS

International Search Report and Written Opinion for PCT/US2017/067596, mailed Mar. 14, 2018, 17 pages.

"Non-Invasive Nasal Airway Remodeling." Aerin Medical, published Sep. 27, 2017 (Retrieved from the Internet Jan. 30, 2020). Internet URL: <https://web.archive.org/web/20170927181830/https://aerinmedical .com/> (Year: 2017).

Dorville, Fabien. "Progress Bar." Behance, published May 3, 2013 (Retrieved from the Internet Jan. 30, 2020). Internet URL: <https://www .behance.net/gallery/8490779/Progress-bar> (Year: 2013).

(56) References Cited

OTHER PUBLICATIONS

Nesmiyanov, Nikita. "12 Open Source/Commercial Control Panels for Virtual Machines (VM's) Management." TecMint, published Jul. 28, 2016 (Retrieved from the Internet Feb. 19, 2020). Internet URL: <https://www.tecmint.com/opensource-commercial-control-panels-manage-virtual-machines/> (Year: 2016).
Extended European Search Report for Application No. 21172211.1, mailed Dec. 10, 2021, 7 pages.
Buckley et al., "High-resolution spatial mapping of shear properties in cartilage," J Biomech., Mar. 3, 2010;43(4):796-800, Epub Nov. 5, 2009.
Buckley et al., "Mapping the depth dependence of shear properties in articular cartilage," J Biomech., 41(11):2430-2437, Epub Jul. 10, 2008.
Cole, "Biophysics of nasal airflow: a review," Am J Rhinol., 14(4):245-249, Jul.-Aug. 2000.
Cole, "The four components of the nasal valve," Am J Rhinol., 17(2):107-110, Mar.-Apr. 2003.
Fang et al., "Nasal Endoscopic Surgery Combined with Multisite Radiofrequency Technology for Treating Perennial Allergic Rhinitis," J First Mil Med Univ, vol. 25 No. 7, pp. 876-877, 2005.
Griffin et al., "Effects of enzymatic treatments on the depth-dependent viscoelastic shear properties of articular cartilage," J Orthop Res., 32(12):1652-1657, Epub Sep. 5, 2014.
Kjaergaard et al., "Relation of nasal air flow to nasal cavity dimensions," Arch Otolaryngol Head Neck Surg., 135(6):565-570, Jun. 2009.
Liu et al., "Impact of radiofrequency thermocoagulation of bilateral vidian and anterior ethmoidal nerve cluster regions on nasal mucociliary transport function in perennial allergic rhinitis and vasomotor rhinitis," China Journal of Endoscopy, vol. 14, No. 11, 12 pages, Nov. 2008.
Silverberg et al., "Structure-function relations and rigidity percolation in the shear properties of articular cartilage," Biophys J., 107(7):1721-1730, Oct. 7, 2014.
Stewart et al., "Development and validation of the Nasal Obstruction Symptom Evaluation (NOSE) scale," Otolaryngol Head Neck Surg., 130(2):157-163, Feb. 2004.
Stupak, "A Perspective on the Nasal Valve," Dept. of Otorhinolaryngology, Albert Einstein College of Medicine, Nov. 6, 2009.
Stupak, "Endonasal repositioning of the upper lateral cartilage and the internal nasal valve," Ann Otol Rhinol Laryngol., 120(2):88-94, Feb. 2011.
International Search Report and Written Opinion for PCT/US2012/042316, mailed Aug. 24, 2012, 15 pages.
International Search Report and Written Opinion for PCT/US2014/054726, mailed Dec. 23, 2014, 5 pages.
International Search Report and Written Opinion for PCT/US2015/023742, mailed Jun. 29, 2015, 5 pages.
Singapore Search Report for Application Serial No. 201309238-2, mailed Apr. 17, 2014, 27 pages.
Supplementary European Search Report for U.S. Appl. No. 15/772,528, mailed Sep. 26, 2017, 7 pages.
Search Report in European Application No. 18204723.3 dated Feb. 18, 2019, 8 pages.
Extended European Search Report for Application No. 19199126.4, mailed Dec. 9, 2019, 6 pages.
Extended European Search Report for App. No. 19159707.9, mailed Nov. 9, 2019, 7 pages.
Extended European Search Report for App. No. 21172995.9, dated Jul. 9, 2021, 8 pages.
Extended European Search Report for App. No. 23177809.3, mailed Sep. 25, 2023.
Arora et al., "Cryodestruction of Vidian Nerve Branches," Indian J. Otolaryngology, vol. 32, No. 3, Sep. 1980, pp. 80-82.
Back et al., "Submucosal Bipolar Radiofrequency Thermal Ablation of Inferior Turbinates: A Long-Tenn Follow-up with Subjective and Objective Assessment," Laryngoscope, vol. 112, No. 10, Oct. 2002, pp. 1806-1812.
Banhiran et al., "Quality of life in patients with chronic rhinitis after radiofrequency inferior turbinate reduction," J. Med Assoc Thai, vol. 93, No. 8, 2010, pp. 950-957.
Bronzino, Medical Devices and Systems, The Biomedical Engineering Handbook (3rd ed. 2006), Chapter 63, Electrosurgical Devices, pp. 63-1-63-9.
Chen et al., "Preliminary study on radiofrequency thermocoagulation of the posterior inferior nerve, anterior ethmoidal nerve, and inferior turbinate under nasal endoscopy for the treatment of perennial allergic rhinitis," China Journal of Endoscopy, vol. 11, No. 3, Mar. 2005, pp. 239-240 and p. 243 (English Translation).
Chen et al., "Radiofrequency treatment of nasal posterior-under nerve, ethmoidal nerve and infraturbinal for perennial allergic rhinitis under nasal endoscope," China Journal of Endoscopy, vol. 11, No. 3, Mar. 2005, pp. 239-240 and p. 243 (English Translation).
Coste et al., "Radiofrequency Is a Safe and Effective Treatment of Turbinate Hypertrophy," Laryngoscope, vol. 111, No. 5, May 2001, pp. 894-899.
Fang et al., "Nasal Endoscopy Combined with Multiple Radiofrequency for Perennial Allergic Rhinitis," J. First Mil Med Univ, vol. 25, No. 7, 2005, pp. 876-877 (English Translation).
Haemmerich, "Biophysics of Radiofrequency Ablation," Critical Reviews in Biomedical Engineering, vol. 38, No. 1, 2010, pp. 53-63.
Haikou, "Diagnostic Criteria and Efficacy Evaluation Criteria of Allergic Rhinitis," Otorhinolaryngol, vol. 33, No. 3, Jun. 1998, pp. 134-135.
Hong et al., "Radiofrequency Ablation: Mechanism of Action and Devices," J. Vasc. Interv. Radiol., vol. 21, No. 8S, 2010, pp. S179-S186.
Hytönen et al., "Radiofrequency Thermal Ablation for Patients with Nasal Symptoms: A Systematic Review of Effectiveness and Complications," Eur. Arch. Otorhinolaryngol, vol. 266, 2009, pp. 1257-1266.
Ilgner et al., "Feasibility of coblation versus laser resection in recurrent nasal polyps," Proc. of SPIE, vol. 5686, Apr. 25, 2005, pp. 322-327.
Kong et al, "Low-temperature plasma ablation of inferior turbinate for the treatment of perennial allergic rhinitis", J Clin. Otorhinolaryngol., vol. 19, No. 5, Mar. 2005, pp. 214-215 (English Translation).
Kong et al., "Clinical Observation on Radiofrequency Ablation Treatment in Perennial Allergic Rhinitis," J Clin. Otorhinolaryngol., vol. 19, No. 5, Mar. 2005, pp. 214-215 (English Translation).
Konno, "Historical, Pathophysiological, and Therapeutic Aspects of Vidian Neurectomy," Curr. Allergy Asthma Rep., vol. 10, 2010, pp. 105-112.
Koyyalagunta et al., Radiofrequency and Cryoablation for Cancer Pain, Techniques in Regional Anesthesia & Pain Management, vol. 14, No. 1, Jan. 2010, pp. 3-9.
Lee et al., "Surgical Management of Turbinate Hypertrophy in the Office: Three Mucosal Sparing Techniques," Operative Techniques in Ottolaryngology—Head and Neck Surgery, vol. 12, No. 2, Jun. 2001, pp. 107-111.
Levine, "Lasers in Endonasal Surgery," Otolaryngolog. Clinics of N. Am, June, vol. 30, No. 3, Jun. 1, 1997, pp. 451-455.
Liang et al., "Radiofrequency Treatment of Ethmoidal Nerve with Allergic Rhinitis Under Nasal Endoscopy," J. Clint Otorhinolaryngol., vol. 13, No. 8, Aug. 1999, pp. 341-342 (English Translation).
Philippson, "Principles of Electrical Resistance of Living Tissue," Bull. Cl. Sci. Acad. R. Belg., Ser. 5, vol. 7, No. 7, Jul. 1921, pp. 387-403.
Sackenheim, "Radio Frequency Ablation the Key to Cancer Treatment," J. Diagnostic Medical Sonography, vol. 19, No. 2, 2003, pp. 88-92.
Windsor et al., "Sphenopalatine Ganglion Blockage: A Review and Proposed Modification of the Transnasal Technique," Pain Physician, vol. 7, 2004, pp. 283-286.

\* cited by examiner

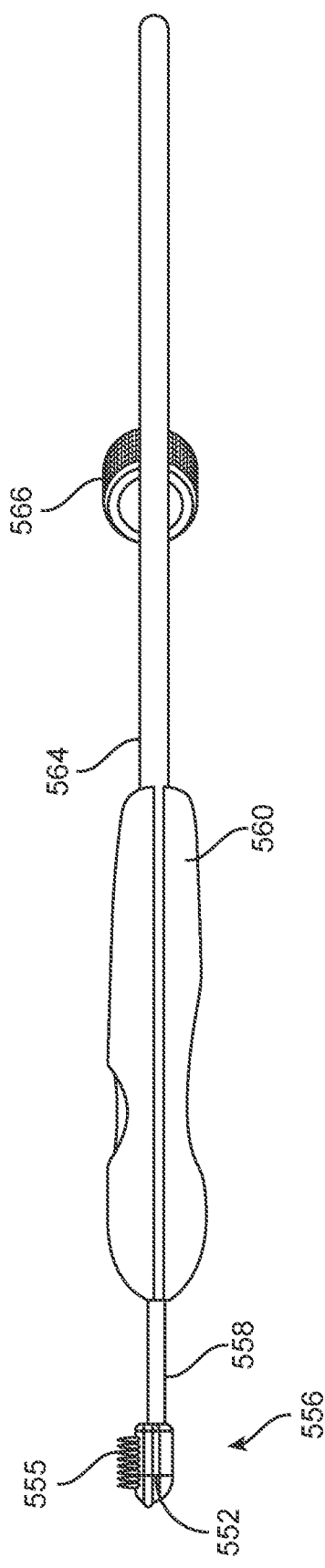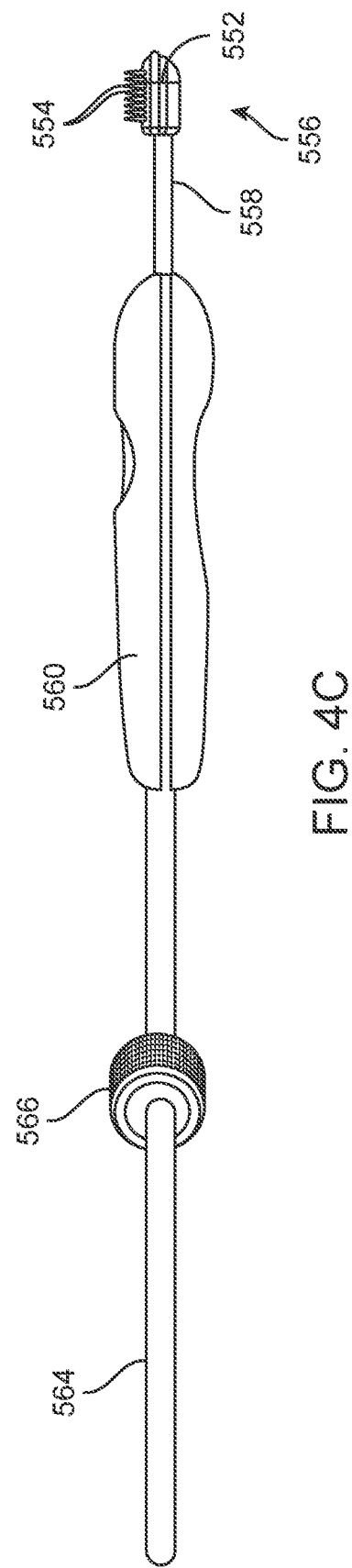
FIG. 4B
FIG. 4C

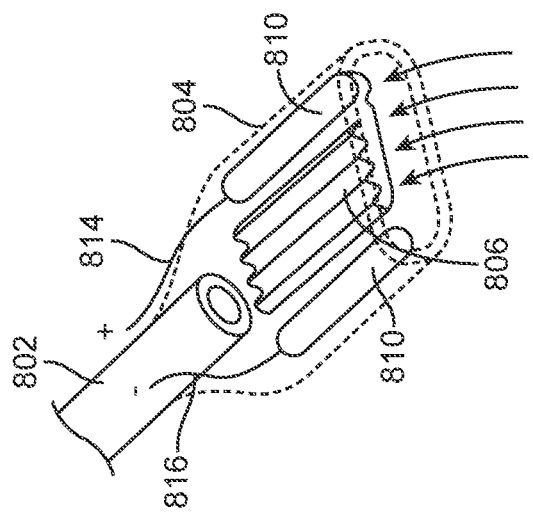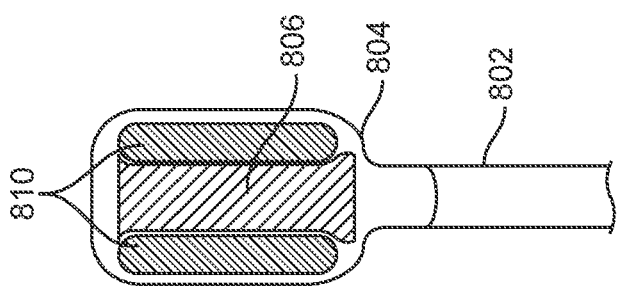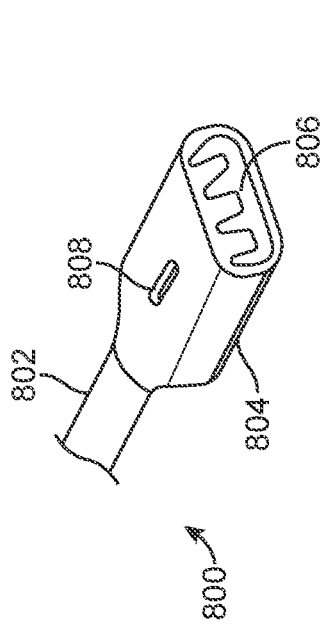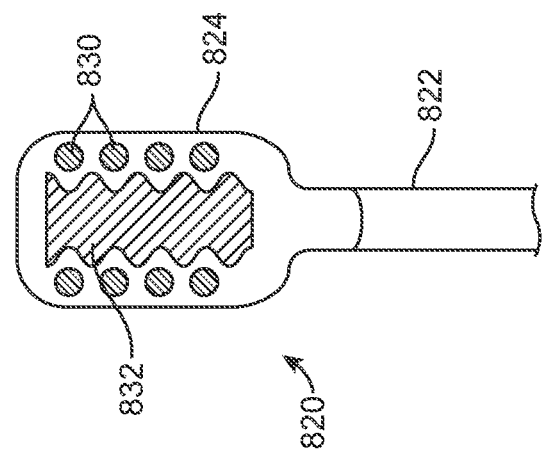

SOFT PALATE TREATMENT

CROSS-REFERENCE TO RELATED APPLICATIONS

This application is a continuation application of U.S. application Ser. No. 15/930,676, filed May 13, 2020, now U.S. Pat. No. 11,806,071, which is a continuation-in-part of U.S. patent application Ser. No. 15/848,951, filed Dec. 20, 2017, now U.S. Pat. No. 11,116,566 which claims the benefit of and priority to U.S. Provisional Patent Application No. 62/438,300, filed Dec. 22, 2016. This application also claims the benefit of and priority to U.S. Provisional Patent Application No. 62/847,438, filed May 14, 2019. The disclosures of the above-referenced applications are hereby incorporated by reference in their entireties.

TECHNICAL FIELD

This application relates generally to the field of medical devices and treatments. In particular, the application relates to systems, devices and methods for treating the soft palate and possibly other parts of the mouth, to improve breathing and specifically to treat snoring and/or sleep apnea.

BACKGROUND

Snoring and sleep apnea are extremely prevalent and significant health issues in the United States and other parts of the world. Sleep apnea is defined as the cessation of breathing during sleep. Obstructive sleep apnea (OSA) is the most common form of sleep apnea, and it is often linked to obesity, which is becoming an ever more prevalent health condition. OSA occurs when the tissues in the back of the throat repetitively collapse during sleep, producing snoring and complete airway blockage. This blockage creates pauses in breathing that occur repeatedly every night. In severe cases, these pauses in breathing can occur as frequently as every thirty seconds—i.e., many times each night. Alarmingly, the pauses can last up to a full minute.

The repetitive pauses in breathing during sleep in an OSA sufferer are accompanied by a reduction in blood oxygen levels and are followed by an arousal response. This response includes a release of substances into the bloodstream, which promotes elevation of blood pressure, inflammation, insulin resistance, and a disruption of the brain wave sleep pattern. The consequences of untreated sleep apnea include poor quality sleep, excessive daytime fatigue and sleepiness, irritability, hard-to-control high blood pressure and diabetes, heart disease and stroke. Moreover, untreated sleep apnea may be responsible for job impairment and motor vehicle crashes.

Snoring, which is typically a less serious and severe condition than sleep apnea, still has significant effects on people who suffer from it and their loved ones. Snoring can affect a person's sleep and of course can also disrupt the sleep of a spouse, sibling or others who are sleeping nearby.

Many different methods and devices have been developed and tested for treating sleep apnea and snoring, but no perfect solution has yet been discovered. Some treatments for sleep apnea involve major, invasive surgery, for example to remove portions of the tongue and/or throat or to place mechanical slings or other implants in the tongue, in an effort to prevent the tongue from falling back in the mouth during sleep. Some patients wear continuous positive airway pressure (CPAP) masks for sleeping, but those devices are obtrusive, loud and uncomfortable, making sleeping difficult and leading to poor patient compliance. Less invasive techniques, such as wearing an adhesive nasal strip to bed each night, are usually less effective or do not work at all, since many OSA patients are either already mouth breathers or convert to mouth breathing when a nasal blockage is addressed.

Therefore, it would be highly advantageous to have improved systems, devices and methods for treating sleep apnea and snoring. Ideally, these improved systems, devices and methods would be relatively less invasive than most of the surgical techniques used currently or tried in the past, while still working effectively for many patients. Also ideally, the improved techniques would not involve implants. The present disclosure will address at least some of these objectives.

BRIEF SUMMARY

Embodiments of the present application are directed to devices, systems and methods for treating the soft palate and possibly other areas of the mouth and/or throat, to treat sleep apnea and/or snoring. Various embodiments may be used to reshape, remodel, strengthen, stiffen and/or otherwise change properties of tissues of the soft palate, including but not limited to skin, muscle, mucosa, submucosa, cartilage, blood vessels and/or nerves of the soft palate. This change (or changes) in the soft palate may prevent collapse of the soft palate and/or vibration of the soft palate during nighttime breathing and thus prevent or at least reduce OSA and/or snoring.

According to one aspect of the present disclosure, a method of treating a soft palate in a patient to treat sleep apnea, snoring or both may involve advancing a treatment element of a treatment device through the patient's mouth, contacting a treatment surface of the treatment element with the soft palate, delivering energy to the soft palate via one or more energy delivery members on the treatment surface, and removing the treatment element from the mouth. In some embodiments, the energy delivery members are two rows of bipolar, radiofrequency electrode pairs protruding from the treatment surface, and delivering the energy involves delivering radiofrequency energy between the two rows of electrode pairs, to reshape, remodel, strengthen and/or change a property of the soft palate.

In some embodiments, the method may also involve applying force against the soft palate with the treatment surface to at least temporarily deform tissue of the soft palate. Some embodiments may also involve forming an incision in mucosal tissue of the soft palate, in which case the energy may be delivered to submucosal tissue. The type of delivered energy may be radiofrequency (monopolar or bipolar), microwave, ultrasound, heat, cryogenic energy (energy removal) or the like. The method may also involve repositioning the treatment element to a new location on the soft palate and repeating the delivering step, before removing the treatment element from the mouth. This may be repeated as many times as desired, to cover a given area of the soft palate.

Optionally, some embodiments may also include injecting a substance into the soft palate before applying energy to the tissue. For example the substance may be an agent that increases conductivity of the tissue or enhances softening, stiffening or other tissue changes. Such an injection may be performed using conventional techniques and device, such as a syringe, or alternatively a treatment device may include a built-in injection device.

In another aspect of the disclosure, a device for treating a soft palate in a patient to treat sleep apnea, snoring or both may include a handle, a shaft, a treatment element, and a connector for connecting the handle with a power source. The shaft may include a distal end with a neck, and the treatment element may extend from the neck and may be angled relative to a longitudinal axis of the shaft. The treatment element may include a treatment surface and at least one energy delivery member on the treatment surface. In some embodiments, the energy delivery member comprises two rows of bipolar, radiofrequency electrode pairs protruding from the treatment surface. The electrodes may be triangular in shape, for example. In some embodiments, the treatment surface has a convex shape for creating a concave deformity in the soft palate. In some embodiments, the device may have multiple shafts and multiple treatment elements, where each of the treatment elements is located on one of the multiple shafts.

In another aspect of the present disclosure, a method of treating a soft palate in a patient may involve advancing a tissue treatment portion of a soft palate treatment device through the patient's mouth, contacting a treatment surface of the tissue treatment portion with mucosal tissue of the soft palate, and delivering energy from the tissue treatment portion through the mucosal tissue to a target tissue in the soft palate beneath to the mucosal tissue, to change at least one property of the target tissue. The method may further involve cooling the mucosal tissue with a cooling member on the treatment surface of the tissue treatment portion and removing the tissue treatment portion from the mouth. In some embodiments, the change in the at least one property of the target tissue results in a reduction of at least one of snoring or sleep apnea in the patient.

In some embodiments, the tissue treatment portion includes two rows of bipolar, radiofrequency electrode pairs on the treatment surface, and delivering the energy involves delivering radiofrequency energy between the two rows of electrode pairs. The method may optionally further involve applying force against the soft palate with the treatment surface while delivering the energy, to deform tissue of the soft palate. In such embodiments, changing the at least one property of the target tissue may involve reshaping the target tissue. In various embodiments, changing the at least one property of the target tissue may involve at least one of reshaping, remodeling, stiffening, strengthening, tightening, shortening, thickening or ablating the target tissue.

According to various embodiments, the delivered energy may be radiofrequency, microwave, ultrasound, heat or cryogenic energy. Optionally, the method may further involve repositioning the tissue treatment portion to a new location on the soft palate and delivering energy to the target tissue again, to form a treatment pattern in the target tissue. In some embodiments, cooling the mucosal tissue involves applying a suction force with the cooling member to suction air through the cooling member. In alternative embodiments, cooling the mucosal tissue involves circulating a cooling fluid through the cooling member.

Optionally, the method may further involve measuring a temperature of the mucosal tissue with a temperature sensing member on the treatment surface of the tissue treatment portion. In various embodiments, the target tissue may be one or more of muscle, cartilage, tendon, ligament, connective tissue, nerve or blood vessel. In one embodiment, the tissue treatment portion is hook-shaped, and contacting the treatment surface involves contacting a superior surface and an inferior surface of the soft palate. Optionally, the method may further include bending a malleable shaft of the soft palate treatment device before advancing the tissue treatment portion. The method may also further involve applying force to the mucosal tissue with the tissue treatment portion to cause the tissue treatment portion to flex at at least one flex point along the tissue treatment portion.

In another aspect of the present disclosure, a device for treating a soft palate in a patient may include a handle, a shaft having a proximal end attached to the handle and a distal end, an elongate treatment element extending from the distal end of the handle, and a connector for connecting the handle with a power source. The elongate treatment element may include a treatment surface, at least two energy delivery members on the treatment surface, and a cooling member on the treatment surface between the at least two energy delivery members.

In some embodiments, the distal end of the shaft has a neck that is angled relative to a longitudinal axis of the shaft, and the elongate treatment element is attached to the neck. In some embodiments, the at least two energy delivery members are two elongate bipolar radiofrequency electrodes. Alternatively, the at least two energy delivery members may be two parallel rows of multiple bipolar radiofrequency electrodes. In some embodiments, each of the radiofrequency electrodes is a protruding, non-penetrating electrode. In some embodiments, the treatment surface has a convex shape for creating a concave deformity in the soft palate.

In some embodiments, the cooling member may include at least one suction port for suctioning air through the cooling member to cool mucosal tissue in contact with the cooling member. In alternative embodiments, the cooling member may include a channel for circulating cooling fluid through the cooling member to cool mucosal tissue in contact with the cooling member. In some embodiments, the elongate treatment element has a hook shape, and the treatment surface is configured to contact a superior surface and an inferior surface of the soft palate. In some embodiments, the shaft is malleable. Optionally, the device may include at least one flex member on a top surface of the elongate treatment element. Also optionally, the device may include a temperature sensing member on the elongate treatment element, for sensing a temperature of mucosal tissue in contact with the treatment surface.

These and other aspects and embodiments are described further below, in relation to the attached drawing figures.

BRIEF DESCRIPTION OF DRAWINGS

Certain embodiments and modifications thereof will become apparent from the detailed description below, having reference to the figures that follow.

FIGS. 4A-4G are various views of a device for applying energy to the soft palate for treating OSA and/or snoring, according to one embodiment;

FIGS. 11A-11C are perspective, bottom and partial cross-sectional views, respectively, of a distal portion of a soft palate tissue treatment device with a cooling member, according to one embodiment;

FIG. 12 is a bottom view of a distal portion of a soft palate tissue treatment device with a cooling member, according to an alternative embodiment;

DETAILED DESCRIPTION

The assignee of the present application has developed a number of devices, systems and methods for delivering energy to tissues in the nasal passages to treat nasal valve insufficiency, chronic nasal congestion, post nasal drip, chronic cough, rhinitis, and other breathing abnormalities and disorders of the nasal passages. The systems generally include an energy delivery console (or "box") and a hand piece (or "stylus") for delivering the therapy to the nasal tissue. The hand piece typically includes a handle, a shaft, and a treatment delivery element at or near the end of the shaft for delivering the energy to the tissues. One general type of embodiment includes one handle, one shaft and one treatment element for advancing through a nostril. Another general type of embodiment includes a clamp-like configuration, with two handles, two shafts and two treatment elements, where tissue is clamped between the two tissue elements, which are either advanced through both nostrils or through one nostril and outside of the nose. Various embodiments may include a clamp with only one active element on one side, alternating and/or intermittent top/bottom electrodes dispersed across the treatment elements, etc. In some embodiments, the method of treatment involves applying force to a tissue to be treated with the treatment element, in some cases to deform the tissue, and applying energy to the tissue with the treatment element. When the treatment is stopped and the treatment element is removed, the target tissue is reformed and/or changed in some other way (ablated, shrunken, stiffened, reduced, etc.) and retains at least some of that change after the treatment is complete. In one embodiment, the treatment element delivers bipolar radiofrequency (RF) energy from multiple electrodes on the treatment element, although many other energy modalities and treatment element configurations are possible.

Patents describing various embodiments of these tissue treatment devices, systems and methods include U.S. Pat. Nos. 8,936,594; 9,237,924; 9,433,463; 9,415,194; 9,452,087 and 9,433,463. All of these patents, referred to herein as "the Incorporated Patents," are hereby incorporated by reference herein in their entireties. Any of the embodiments described in the Incorporated Patents may be used or adapted for use in treating the soft palate and/or other mouth or throat structures to treat OSA and/or snoring. The many embodiments of methods, devices and systems described in the Incorporated Patents will not be repeated in this application, but again, any embodiments described in those patents may be used or adapted for use in performing the methods described herein for treating OSA and/or snoring.

Figure 1:
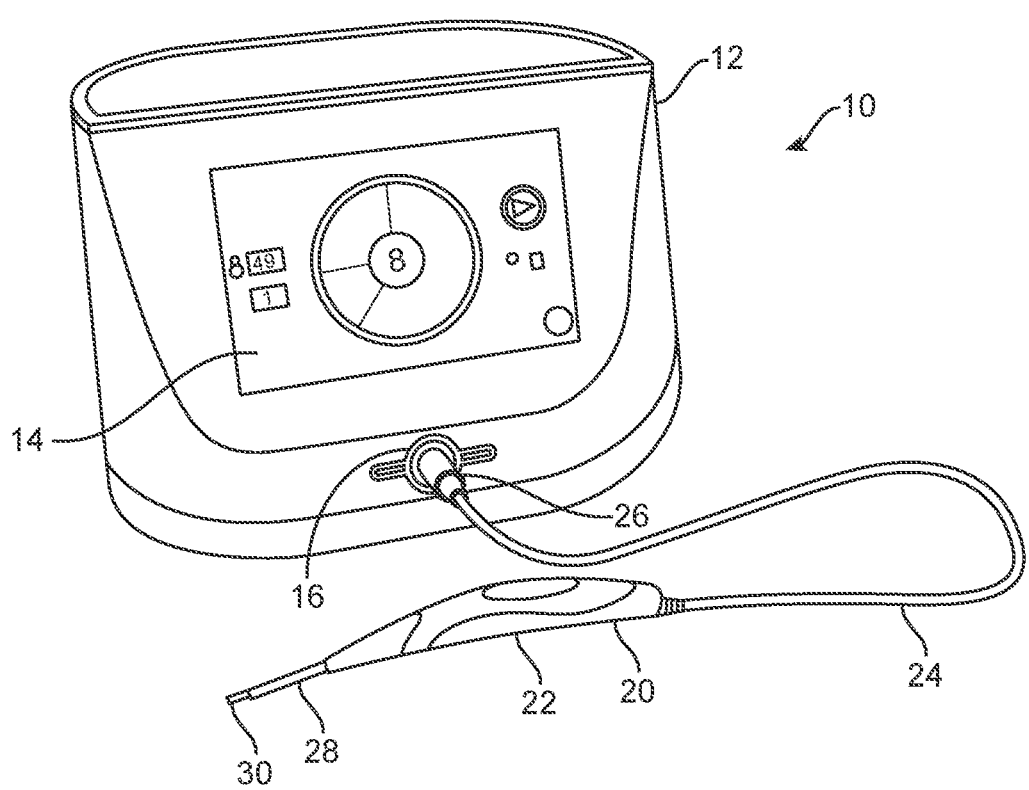
FIG. 1 is a perspective view of the Vivaer® Nasal Airway Remodeling System (Aerin Medical Inc., www.aerinmedical.com), which in some embodiments may be used or adapted for use in treating soft palate tissues.

Referring now to FIG. 1, a perspective view of the Vivaer® Nasal Airway Remodeling System 10 (or "treatment system 10"), patented by the assignee of the present application, is illustrated. (See www.aerinmedical.com.) Treatment system 10 includes a console 12 (or "energy source") and a stylus 20 (or "treatment device," "treatment member" or the like). Similarly, the various embodiments of the soft palate treatment system described below also include a console and stylus. Furthermore, in some embodiments, treatment system 10 may be used (or adapted for use) to treat soft palate tissue. For example, in some embodiments, stylus 20 of FIG. 1 may be used to treat soft palate tissue, while in alternative embodiments, a different stylus, designed specifically for treating soft palate tissue, may be used with console 12. In the illustrated embodiment, treatment system 10 is designed to deliver bipolar radiofrequency (RF) energy, but in alternative embodiments, system 10 may be designed to deliver monopolar RF, ultrasound, microwave, laser, heat, electrical, chemical, pharmaceutical and/or any other type of energy or combination of energy modalities. Alternative embodiments may be designed to remove energy, via cryogenic therapy or other cooling techniques. Console 12 generally includes a housing with a display 14, an outlet 16 for plugging in stylus 20, and a power cord (not shown) for connecting with a power source (e.g., a wall outlet). A detailed description of the console 12 may be found in U.S. patent application Ser. No. 16/668,678, filed Oct. 30, 2019, which is hereby incorporated by reference and included as one of the Incorporated References.

Stylus 20 generally includes a handle 22, a cable 24, an adapter 26, a shaft 28 and a treatment element 30. Details of various embodiments of stylus 20 will be described below and are further described in the Incorporated Patents. To adapt treatment system 10 for use in the soft palate, one or more of a number of different alterations may be made to system 10. For example, shaft 28 could be made longer, could be made malleable for angle adjustment, or could be pre-formed with an angle or bend. Treatment element 30 could be made longer and/or wider, could be made to have a different overall shape and/or could be angled. Treatment algorithms designed into console 12, if any, may be configured especially for soft palate treatment. These and/or other changes may be made to system 10, to enhance its ability to treat soft palate tissue, according to various alternative embodiments.

Figure 2:
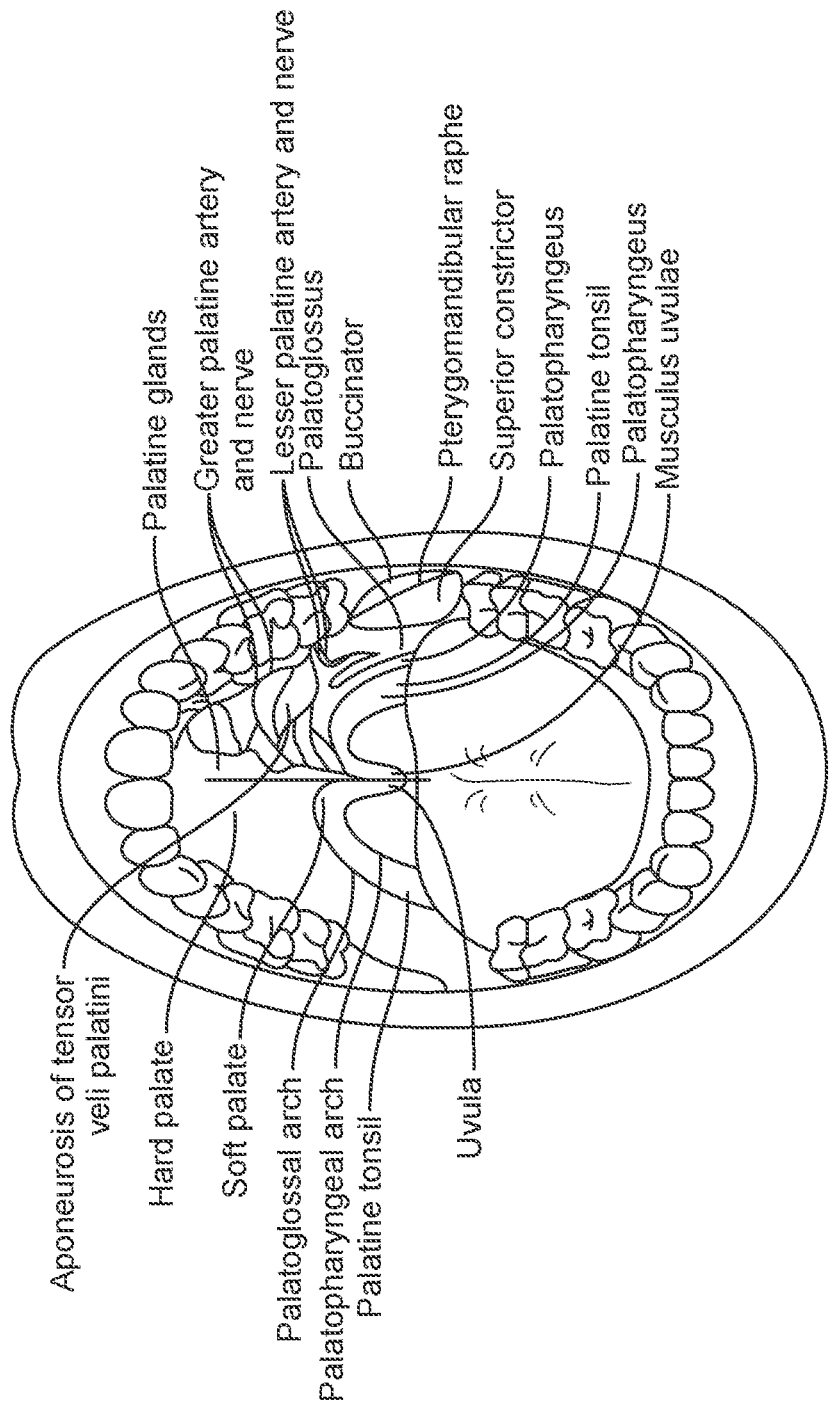
FIG. 2 is a front view of an open mouth, with mucosal tissue along one side of the hard palate and the soft palate removed, to show various structures of the hard and soft palate.
Figure 3:
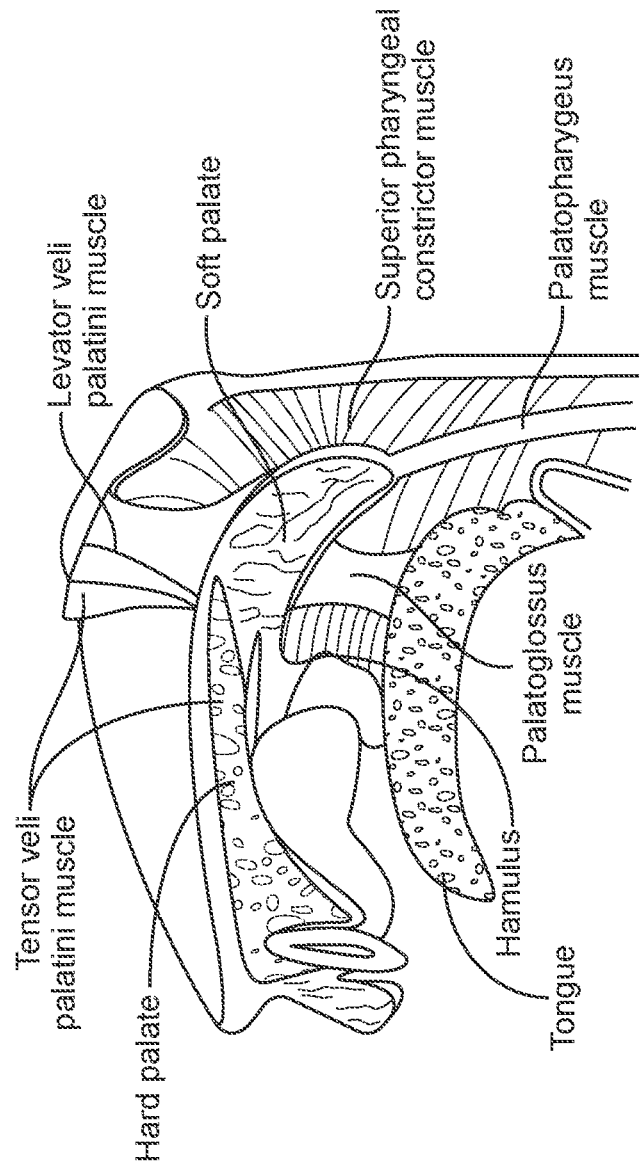
FIG. 3 is a side, cross-sectional view of a portion of a mouth, showing the various muscles that make up the soft palate.

Referring now to FIGS. 2 and 3, two anatomical drawings of the soft palate are provided. FIG. 2 is a front view of an open mouth. FIG. 3 is a lateral, cross-sectional view of a portion of an oral cavity, illustrating the soft palate. As can be seen in both figures, the hard palate extends from the top teeth posteriorly and medially, toward the back of the mouth. The soft palate extends in a posterior direction from the hard palate. As best seen in FIG. 2, the uvula extends from the middle of the posterior edge of the soft palate, and the tonsils are located near the lateral edges of the soft palate on both sides. The soft palate is made up of five muscles, covered in mucosal tissue, which play important roles in swallowing and breathing. As best seen in FIG. 3, the five muscles of the soft palate are the tensor veli palatini, the palatoglossus, the palatopharyngeus, the levator veli palatini, and the musculus uvulae (FIG. 2). These muscles work together to suspend and move the soft palate as needed, to facilitate breathing, swallowing and sneezing.

In some patients with sleep apnea, the palatopharyngeus muscle tends to collapse into the airway. One treatment that has been described for sleep apnea is a surgical procedure, in which the surgeon cuts each of the two palatopharyngeus muscles at the bottom, pulls them up and forward, and stitches them to the upper lateral edges of the pharynx. This acts like a sling for the soft palate. Although this surgery may work well in some patients, it requires general anesthesia and involves an invasive surgical procedure with painful post-surgical recovery.

Methods and devices described below for treating the soft palate may work by stiffening, strengthening, tightening, shortening, ablating and/or otherwise changing any property or properties of one or more of the tissues (muscle, mucosa, nerve, etc.) that make up the soft palate. In some embodiments, for example, energy may be directed at one or more of the muscles that make up the soft palate, to change one or more properties of the muscle and thus treat the soft palate in a way that ameliorates sleep apnea and/or snoring. For example, in various embodiments, the palatopharyngeus muscles may be tightened, stiffened, shortened and/or strengthened, to mimic the surgical procedure described immediately above. In other embodiments, an energy delivery procedure may be directed at the levator veli palatini muscle, instead of the palatopharyngeus. Different muscles or groups of muscles may be treated, according to different embodiments. In yet other embodiments, alternative or additional types of tissues may be targeted, such as nerve or mucosa.

According to various embodiments, some of which are described further below, a treatment of the soft palate may involve delivery of energy to tissue, removal of energy from tissue (e.g., cryotherapy or other cooling techniques), and/or application of pressure to tissue. In embodiments where energy is delivered, the form of energy may be any suitable form, such as but not limited to radiofrequency (RF), heat, electrical, ultrasound, microwave, laser, chemical or the like. In embodiments where energy is removed, any form of cryotherapy or other cooling technique may be used. In addition to energy delivery, some embodiments involve applying pressure to tissue with the treatment element of the treatment device. In many embodiments, the same treatment element used for delivering (or removing) energy will be used for applying pressure. Alternatively, separate components of a device may deliver energy and apply pressure. The pressure applying treatment element may have a shape designed to confer a corresponding shape to the tissue being treated. For example, in some embodiments the tissue treatment surface of the treatment element may have a convex shape, which gives a target tissue a concave shape when pressed against it. Using a shaped treatment element to temporarily change a shape of a target tissue and then delivering energy to (or removing energy from) the target tissue while in the changed shape, may cause a permanent reshaping of the tissue after the treatment is completed. In alternative embodiments, however, little or no pressure may be applied, and energy delivery (or removal) may work by itself on the target tissue(s) to achieve the desired result. These techniques and variations thereon are described further below.

Referring now to FIGS. 4A-4G, further details of one embodiment of a treatment device 550 (or "stylus") will now be described. Further detail may also be found in the Incorporated Patents. Treatment device 550 may be compatible for use with console 12 of FIG. 1 or any other suitable console device. Treatment device 550 may include a handle 560, a shaft 558, and a treatment element 552 that is attached to (or simply a distal portion of) at a distal tip 556 of device 550. Treatment element 552 may be provided on an enlarged distal tip 556 of elongate shaft 558, and as in the embodiment illustrated, may have a convex shape configured to press against and create a concavity in the soft palate tissue, such as cartilage and mucosa. Treatment element 552 may include two rows of protruding RF electrodes 554 and a thermocouple 555 (best seen in FIGS. 4D and 4G). In this embodiment, electrodes 554 are shown as needle electrodes, but in alternative embodiments, electrodes 554 may be protruding but not piercing, for example semicircular bumps, bumps having other shapes such as rectangular or triangular, ridges having any suitable shape and/or pattern, or the like. Other embodiments may include non-protruding electrodes that are flat and/or flush with the tissue contact surface of the treatment element 552. Thus, in various embodiments, electrodes 554 may deliver energy directly to mucosal tissue, to one or more tissues underlying the mucosal tissue, or both. The underlying tissue may be cartilage, nerve, muscle, blood vessel, any combination thereof, or any other suitable tissue.

Handle 560 may include an input control, such as a power button 562, on its front side, which may be used to activate and deactivate treatment element 522. Power button 562 may be positioned in a recess of the handle to allow for finger stability when activating and deactivating the electrode. In other embodiments, the input control may be alternatively or additionally provided in the form of a switch, dial or foot pedal.

Treatment device 550 may either include a generator or be connected to a remote generator. Treatment device 550 may include a flexible wire or cable 564 that connects to an adaptor 566 that is configured to be plugged into a remote generator (not shown). Adaptor 566 may allow transmission of treatment energy between a remote generator and treatment device 550. Adaptor 566 may also allow transmission of any sensor signals between treatment device 550 and a generator or control unit. Treatment device 550 may be provided in a system or kit, including a console (or "generator," "remote generator" or the like (as illustrated in FIG. 1)). The system or kit (with or without the remote generator) may also include a grounding device and/or a cooling device. In some embodiments, the kit includes a positioning element (e.g., a "cottle" device) configured to help a user locate the optimal treatment area.

In various embodiments, shaft 558 has a diameter of about 0.2 inch to about 0.5 inch and a length of about 1.5 inches to about 6 inches. In some embodiments, the shaft and/or handle is made of a polymer, such as polycarbonate or PEEK. In other embodiments, the shaft is made of stainless steel or other metals. The metals may be coated with an external and/or internal insulating coating (e.g., polyester, polyolefin, etc.). Handle 560 may be made of the same material as shaft 558, in some embodiments. In some embodiments, the shaft 558 is rigid. This may allow a user of treatment device 550 increased control over the deformation of soft palate tissue. In other embodiments, shaft 558 may be flexible or malleable. This flexibility or malleability may allow a user adjust an angle of distal tip 556 by bending shaft 558. In some embodiments, the tip-to-shaft angle may be adjustable by way of a locking hinge or other similar mechanism. In some embodiments, distal tip 556 may be flexible or pre-curved along its length, so that it better conforms to the tissue of the soft palate. Deformability may also be provided by the geometry of the device, in addition to materials. For instance, laser cutting slots into distal tip 556 and/or the shaft 558 may allow the remaining sections of metal to plastically deform.

Figure 4A:
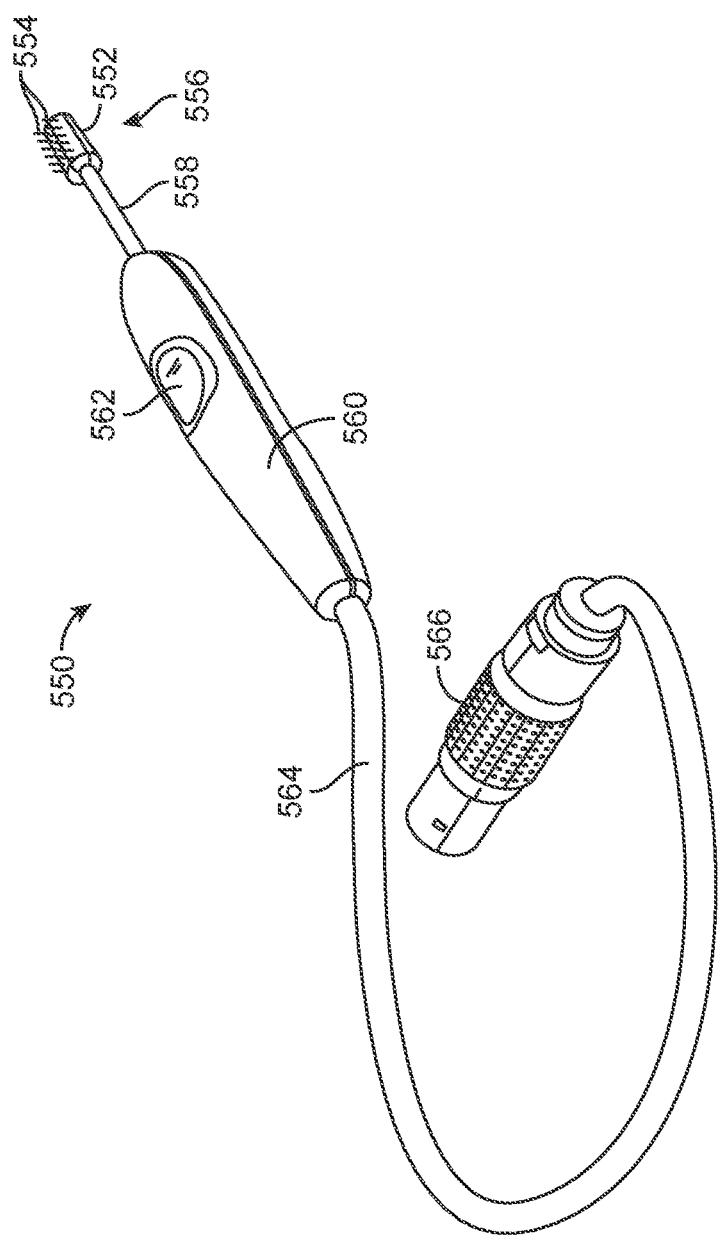
Figure 4D:
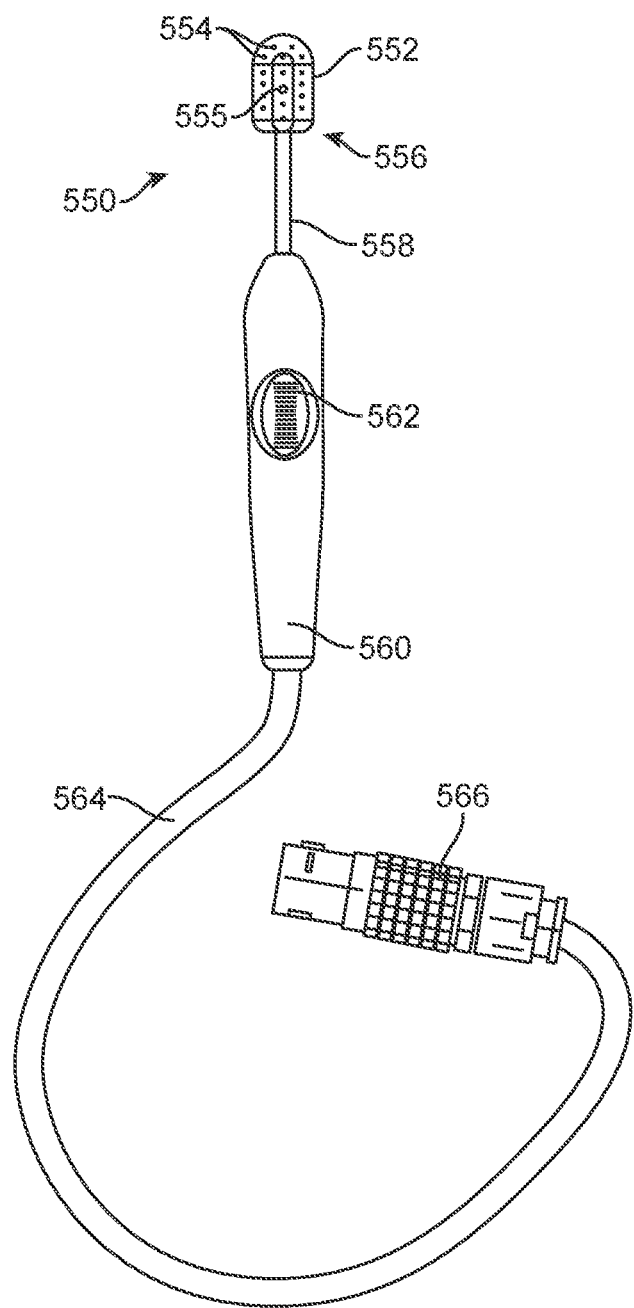
Figure 4E:
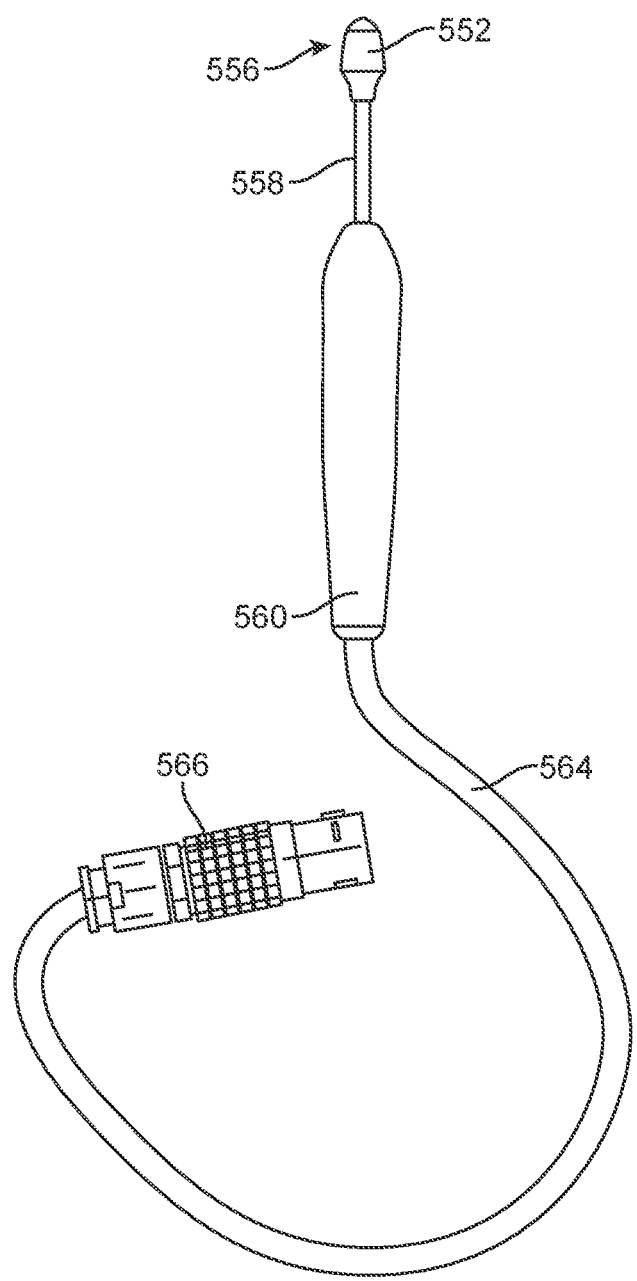
Figure 4F:
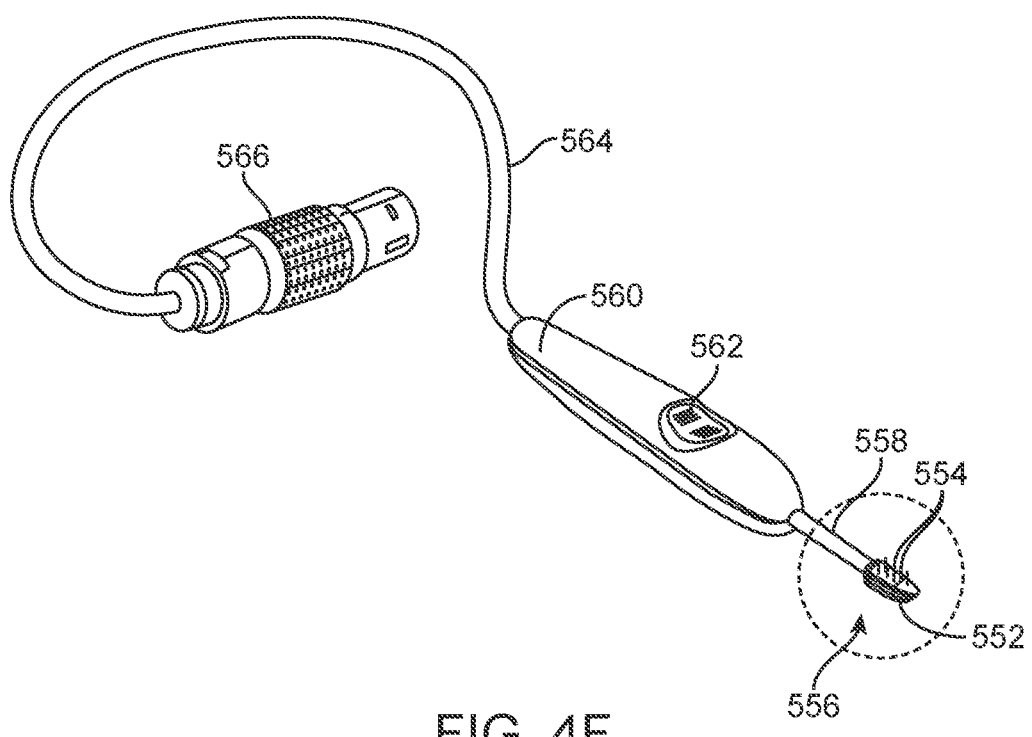

FIGS. 4B and 4C depict side views of treatment device 550. FIGS. 4D and 4E depict front and back views, respectively, of treatment device 550. As shown in FIGS. 4D and 4E, handle 560 generally comprises a rounded elongate shape. Other shapes are also possible. For example device 550 may have a square-shaped cross section. In some embodiments, a circumference (or width or cross-sectional area) of handle 560 may increase distally along the length of handle 560.

Figure 4G:
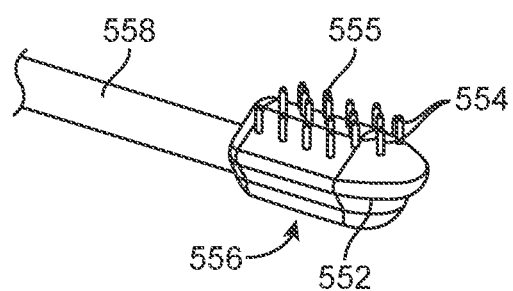

FIG. 4G depicts a larger view of distal tip 556 of device 550. As shown best in FIG. 4G, treatment element 552 comprises a generally elongate shape. The front (or "tissue contact surface") of treatment element 552 comprises a shallow curved surface, providing a convex shape configured to deform the soft palate tissue and create a concavity therein. In alternative embodiments, the front of treatment element 552 may have a concave shape or a flat shape. The shape of the front surface of treatment element 552 may be selected to conform to the soft palate tissue. The back surface of treatment element 552 comprises a shallow curved surface along most of its length. As best seen in FIGS. 4B and 4C, the back surface narrows distally along the length of the element 552, from approximately the distal end of the needle electrodes to the distal tip of the treatment element 552. This shape may maximize visualization of the area to be treated, while, at the same time, providing sufficient rigidity for treatment. Other shapes are also possible. For example, treatment element 552 may have a generally spherical or cylindrical shape. In some embodiments, treatment element 552 comprises an angular shape (e.g., triangular, conical), which may allow for close conformation to the tissue structures.

Treatment element 552 may include a monopolar or bipolar array of RF needles 554. In bipolar embodiments, RF energy is delivered between pairs of needles 554. In monopolar embodiments, RF energy is delivered between needles 554 and a remote grounding pad (not shown). In some embodiments, electrode needle pairs 554 are arranged horizontally across treatment element 552. In some embodiments, electrode needle pairs 554 are arranged vertically across treatment element 552, or along the direction of shaft 558 and handle 560. Other configurations are also possible. For example, needle pairs 554 may be arranged diagonally across treatment element 552. According to alternative embodiments, treatment element 552 may be placed either internally, with needle pairs 554 positioned transmucosally, or externally, with needle pairs 554 positioned transdermally. Distal tip 556 of treatment device 550 may also function as a mold or molding element. In various embodiments, RF energy may be selectively delivered between certain sets of needles to optimize the treatment effect.

Treatment element 552 of the treatment device 550 further comprises a pin-shaped structure comprising a thermocouple 555 within an insulating bushing extending through a middle portion of the front surface of the treatment element 552. In some embodiments, different heat sensors (e.g., thermistors) may be used. In some embodiments, thermocouple 555 may be configured to measure a temperature of the surface or subsurface of tissue to be treated or tissue near the tissue to be treated. A pin shape having a sharp point may allow the structure to penetrate musocal tissue to obtain temperature readings from below the tissue surface. Thermocouple 555 can also be configured to measure a temperature of the treatment element 552. The temperature measurements taken by thermocouple 555 can be routed as feedback signals to a control unit, and the control unit can use the temperature measurements to adjust the intensity of energy being delivered through electrodes 554. In some embodiments, thermocouple 555 or other sensing devices may be used to measure multiple tissue and device parameters. For example, multiple thermocouples 555 or thermistors may be used to measure a temperature at different locations along the treatment element. In some embodiments, one of the sensors may be configured to penetrate deeper into the tissue to take a measurement of a more interior section of tissue. For example, treatment device 550 may have multiple sensors configured to measure a temperature at the mucosa, the cartilage, and/or treatment element 552. As described above, in some embodiments, the sensors described herein are configured to take a measurement of a different parameter. For example, tissue impedance can be measured through the electrodes or one or more separate sensors. These measurements can be used to adjust the intensity and/or duration of energy being delivered through the treatment element. This type of feedback may be useful from both an efficacy and a safety perspective.

In various embodiments, treatment element 552 may have any suitable size and shape. For example, in some embodiments, treatment element 552 may have a width of about 0.2 inch to about 1 inch and a length of about 0.4 inch to about 3 inches. Treatment element 552 can, in some embodiments, comprise a ceramic material (e.g., zirconium, alumina, silicon glass). Such ceramics may advantageously possess high dielectric strength and high temperature resistance. In some embodiments, treatment element 522 may include polyimides or polyamides, which may advantageously possess good dielectric strength and elasticity and be easy to manufacture. In some embodiments, treatment element 552 may include thermoplastic polymers. Thermoplastic polymers may advantageously provide good dielectric strength and high elasticity. In some embodiments, treatment element 552 may include thermoset polymers, which may advantageously provide good dielectric strength and good elasticity. In some embodiments, treatment element 552 may include glass or ceramic infused polymers. Such polymers may advantageously provide good strength, good elasticity, and good dielectric strength.

In some embodiments, electrodes 554 have a diameter of about 0.15 inch to about 0.25 inch and a length of about 0.2 inch to about 0.5 inch. In some embodiments, electrodes 554 may be made of steel (e.g., stainless, carbon, alloy). Steel may advantageously provide high strength while being low in cost and minimally reactive. In some embodiments, electrodes 554 or other energy delivery elements described herein comprise materials such as platinum, gold, or silver. Such materials may advantageously provide high conductivity while being minimally reactive. In some embodiments, electrodes 554 or other energy delivery elements described herein may include titanium, which may advantageously possess a high strength to weight ratio and be highly biocompatible. In some embodiments, electrodes 554 or other energy delivery elements described herein may include nickel titanium alloys. These alloys may advantageously provide high elasticity and be biocompatible. Other similar materials are also possible.

Energy applied to the tissue to be treated using any combination of the embodiments described in this application may be controlled by a variety of methods. In some embodiments, temperature or a combination of temperature and time may be used to control the amount of energy applied to the tissue. Tissue is particularly sensitive to temperature, so providing just enough energy to reach the target tissue may provide a specific tissue effect, while minimizing damage resulting from energy causing excessive temperature readings. For example, a maximum temperature may be used to control the energy. In some embodiments, time at a specified maximum temperature may be used to control the energy. In some embodiments, thermocouples, such as those described above, are provided to monitor the temperature at the electrode and provide feedback to a control unit. In some embodiments, tissue impedance may be used to control the energy. Impedance of tissue changes as it is affected by energy delivery. By determining the impedance reached when a tissue effect has been achieved, a maximum tissue impedance can be used to control energy applied.

In the embodiments described herein, energy may be produced and controlled via a generator that is either integrated into the electrode hand piece or is part of a separate assembly that delivers energy or control signals to the hand piece via a cable or other connection. In some embodiments, the generator is an RF energy source configured to communicate RF energy to the treatment element. For example, the generator may comprise a 460 KHz sinusoid wave generator. In some embodiments, the generator is configured to run between about 1 and 100 watts. In some embodiments, the generator is configured to run between about 5 watts and about 75 watts. In some embodiments, the generator is configured to run between about 10 watts and about 50 watts. In some embodiments, the RF energy source may be the same as or similar to the console described in U.S. Patent Application Ser. Nos. 62/753,469, 26/668,608 and 26/668,605, the disclosures of which are hereby incorporated fully by reference.

In some embodiments, the energy delivery element comprises a monopolar electrode. Monopolar electrodes are used in conjunction with a grounding pad. The grounding pad may be a rectangular, flat, metal pad. Other shapes are also possible. The grounding pad may comprise wires configured to electrically connect the grounding pad to an energy source (e.g., an RF energy source). In alternative embodiments, any other suitable form of energy may be substituted for, or combined with, RF energy, such as but not limited to any energy in the electromagnetic spectrum, ultrasound, microwave, laser light, heat, steam, chemical energy, mechanical energy, or the removal of energy, such as cryotherapy devices.

In some embodiments, the treatment/energy delivery element, such as the electrodes described above, may be flat. Other shapes are also possible. For example, the energy delivery element can be curved or comprise a complex shape. For example, a curved shape may be used to place pressure on/deform the tissue to be treated. The energy delivery element may comprise needles or microneedles. The needles or microneedles may be partially or fully insulated. Such needles or microneedles may be configured to deliver energy or heat to specific tissues while avoiding tissues that should not receive energy delivery.

In some embodiments, the non-electrode portion of treatment element 552 may include an insulating material, such as a ceramic material (e.g., zirconium, alumina, silicon glass). In some embodiments, treatment elements 552 may include an insulating material interposed between multiple electrodes 554 or electrode sections. These insulating sections may provide an inert portion of the treatment element that does not deliver energy to the tissue. Such ceramics may advantageously possess high dielectric strength and high temperature resistance. In some embodiments, the insulators described herein comprise polyimides or polyamides, which may advantageously possess good dielectric strength and elasticity and be easy to manufacture. In some embodiments, the insulators described herein comprise thermoplastic polymers. Thermoplastic polymers may advantageously provide good dielectric strength and high elasticity. In some embodiments, the insulators described herein comprise thermoset polymers, which may advantageously provide good dielectric strength and good elasticity. In some embodiments, the insulators described herein comprise glass or ceramic infused polymers. Such polymers may advantageously provide good strength, elasticity, and dielectric strength. In some embodiments, one or more clear materials may be used to make the treatment element 552, to allow at least some visualization of tissue through the device.

In some embodiments, handle 560 and/or shaft 558 may include the same materials as those described with respect to the insulators. In some embodiments, handle 560 and/or shaft 558 may include a metal, such as stainless steel. In other embodiments, handle 560 and/or shaft 558 may include a polymer, such as polycarbonate. Other metals and polymers are also contemplated.

In some embodiments, device 550 may be used in conjunction with a positioning element that can be used to aid in positioning of the device. The positioning element may be integrated into the device itself or can be separate. The positioning element may be used to determine the optimal placement of the device to achieve maximal increase in efficacy. In some embodiments, a positioning element is configured to be inserted and manipulated within the mouth until the patient reports a desired improvement in breathing. Device 550 may then be used to treat, while the positioning element is holding the mouth in the desired configuration. In some embodiments, molds described herein may be used for the same purpose.

In some embodiments, a positioning element may include a shaft, including measurement marks indicating depth. For example, a physician may insert this element into the mouth to manipulate the tissue to find the depth of treatment at which the soft palate is contacted. The positioning element may also comprise marks indicating angle of insertion. The physician may then use the measurement marks to guide insertion of the treatment element to the same spot.

Any of the embodiments of devices described herein may be configured to heat specific tissue while maintaining lower temperatures in other adjacent tissue. The soft palate is an example of a tissue complex that includes adjacent tissues that may benefit from being maintained at different temperatures. Other examples include skin, which includes epidermis, dermis, and subcutaneous fat, and tonsils, which include mucosa, glandular tissue, and vessels. Treatment of other tissue complexes is also possible. For example, in some embodiments, the internal structures of the nasal valve may be heated, while maintaining a lower temperature in the mucosal lining of the mouth and/or skin. In other embodiments, the mucosa may be heated, while maintaining lower temperatures in the skin. Limiting unwanted heating of non-target tissues may allow trauma and pain to be reduced, may reduce scarring, may preserve tissue function, and may also decrease healing time. Combinations of heat transfer and/or heat isolation may allow directed treatment of specific tissue such as cartilage, while excluding another tissue, such as mucosa, without surgical dissection.

Figure 5:
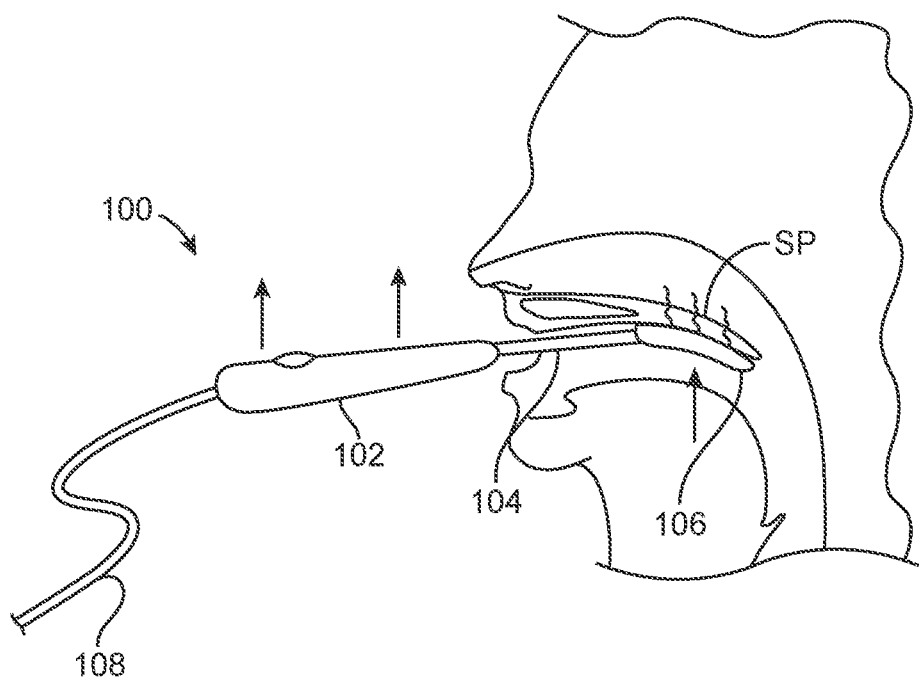
FIG. 5 is a side/cross-sectional view of a patient's head and a side view of a device being applied to the soft palate to treat OSA and/or snoring, according to one embodiment.

Referring now to FIG. 5, one embodiment of a method for treating soft palate SP tissue is illustrated. In the embodiment shown, a soft palate tissue treatment device 100 includes a handle 102, a shaft 104, a treatment element 106 and a cord 108, which is attached to a console (not illustrated). In use, treatment element 106 is advanced into the patient's mouth, and an upper surface (or "treatment surface") of treatment element 106 is contacted with the mucosal surface (or "mucosa") of the soft palate. In some embodiments, the physician or physician's assistant may apply upwardly directed force (solid-tipped arrows) to treatment element 106, by pulling up on handle 102, thus deforming a portion of the soft palate SP. While holding the soft palate in the deformed configuration, energy (wavy lines) may be delivered to the tissue via multiple RF electrodes or other energy delivery devices on the upper, treatment surface of treatment element 106. Force and energy may be applied in any suitable amount and for any suitable length of time, according to treatment goals, patient anatomy, treatment protocols and/or the like. In some embodiments, device 100 may be removed from the patient's mouth after one area of the soft palate is treated. Alternatively, after a first treatment, treatment element 106 may be moved to a second area of treatment, and another treatment may be delivered. This may be repeated as many times as desired, to cover a desired treatment area.

As mentioned above, the treatment may be used to change the shape, strength, stiffness or any other property of any soft palate tissue, such as but not limited to muscle, mucosa, nerve, blood vessel, cartilage and collagen. In embodiments where the shape of the soft palate is changed during the treatment, at least some of this change in shape will be retained after the treatment. In addition to treating the soft palate, some treatment method embodiments may also include treating other nearby tissues of the mouth, throat, tongue, etc. Also, the upper, treatment surface portion of treatment element 106 may include any suitable energy delivery device and may have any suitable shape for addressing the soft palate. For example, treatment element 106 may deliver energy in the form of bipolar RF, monopolar RF, ultrasound, cryotherapy (energy removal), heat, chemical, microwave, laser or any other suitable type of energy, and it may include any number of energy delivery members. The shape of the treatment surface may be convex, concave or flat and may have any shape, such as ovoid, rectangular, triangular, asymmetric, etc.

Figure 6:
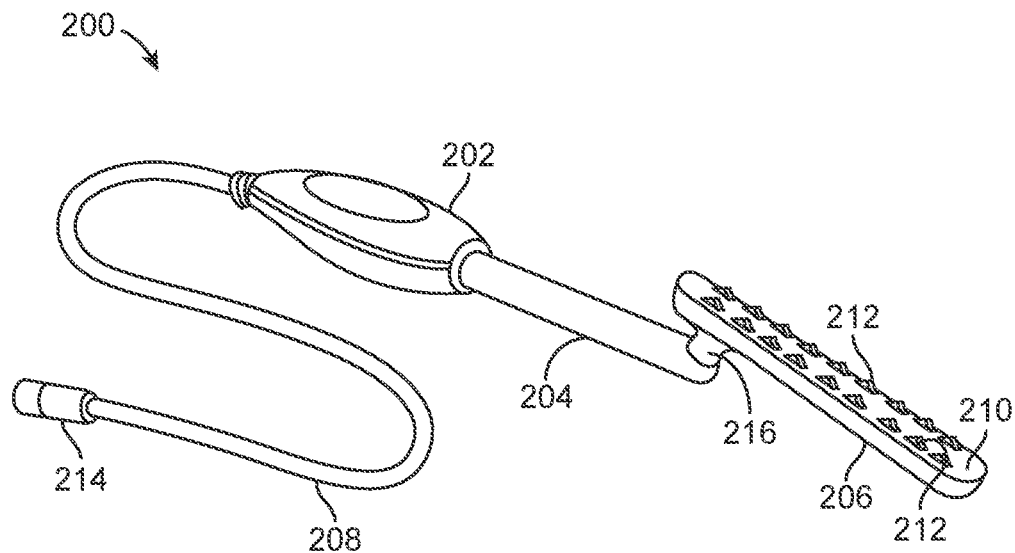
FIG. 6 is a perspective view of a device for applying energy to the soft palate for treating OSA and/or snoring, according to an alternative embodiment.

Referring to FIG. 6, an alternative embodiment of a soft palate treatment device 200 may include a handle 202, a shaft 204, an elongate treatment element 206, a power/energy delivery cable 208, and an adapter 214 for connecting with a console or other power/energy source (not shown). In this embodiment, shaft 204 may include an angled neck 216, so that treatment element 206 is angled slightly, relative to the longitudinal axis of shaft 204. Alternatively, treatment element 206 may be parallel with shaft 204, coaxial with shaft 204, or have any other position relative to shaft 204. Treatment element 206 may include an upper treatment surface 210 and multiple RF electrodes 212 arrayed along surface 210 in two parallel rows. In this embodiment, surface 210 is relatively long and straight, with curved ends, and electrodes 212 are shaped as triangular protrusions from surface 210, are aligned in two rows, and are bipolar RF electrodes 212. As mentioned above, in alternative embodiments, treatment element 206, treatment surface 210 and electrodes 212 may have any other suitable shapes, numbers and configurations, and in alternative embodiments, alternative energy delivery members may be used. Handle 202 may either be rigidly or flexibly attached to shaft 204, thus potentially allowing for relative movement between these two components in some embodiments. In some embodiments, shaft 204 is malleable, to allow the physician to bend the shaft 204 to a desired angle. In some embodiments, electrodes 212 may be moveable, relative to treatment element 206, for example in and out of surface 210 or along surface 210.

As illustrated, in this embodiment, treatment surface 210 is relatively long and flat. This shape may be ideal for treating soft palate (and possibly other tissue in the mouth or throat) to treat OSA and/or snoring. On the other hand, treatment surface 210 may have a convex shape or other shape in alternative embodiments, to help deform soft palate tissue into a desired configuration. Whatever the shape of surface 210, electrodes 212 are used to apply RF energy to the target tissue, to cause heating and eventual shrinking, stiffening, reshaping and/or other property changes of the soft palate. The resulting treatment effect may include volume reduction, tissue stiffening (higher modulus) and/or stiffening by way of more optimal structure (e.g., arched tissue with a higher second moment of inertia, better bending stiffness, etc.). Radiofrequency energy may be controlled via temperature feedback, such as a thermocouple and RF power controller, and/or may be controlled to impart a specific total energy. Device 200 may also be used with minimal built-in control and applied by the physician under visualization until the intended effect on the target tissue has been achieved. In alternative embodiments, alternate energy sources may include cryogenic surface cooling, combinations of cooling and heating technologies, cauterizing agents, ultrasound or the like.

Figure 7:
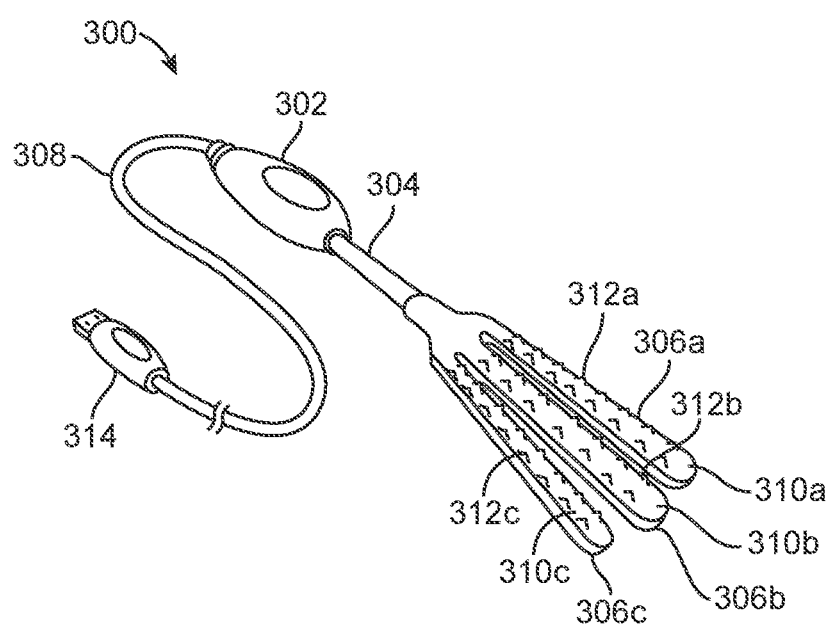
FIG. 7 is a perspective view of a device for applying energy to the soft palate for treating OSA and/or snoring, according to another alternative embodiment.

With reference now to FIG. 7, another alternative embodiment of a soft palate treatment device 300 may include a handle 302, a shaft 304, three treatment elements 306a-c, a power/energy delivery cable 308, and an adapter 314 for connecting with a power/energy source. In this embodiment, shaft 304 is on the same vertical plane as treatment elements 306a-c. Treatment elements 306a-c include upper treatment surfaces 310a-c and multiple RF electrodes 312a-c arrayed along surfaces 310a-c in two parallel rows. This configuration and number of treatment elements 306a-c may be ideal for addressing a larger area of the soft palate in one treatment. Alternative embodiments may include any suitable number, shape, size and configuration of treatment elements and electrodes. For example, either the treatment elements or the electrodes may be formed in cross-cross overlapping configurations, in one or T-shapes, or in any other geometric shape that might facilitate accessing and treating soft palate tissue. In one embodiment, for example, the treatment element (or elements) may be shaped to make a treated-tissue pattern in the soft palate that reduces vibrations. This reduced vibratory effect in the soft palate may help reduce snoring and/or reduce OSA. Again, any suitable pattern, shape, combination of shapes, sizes or the like may be used in a given embodiment.

As mentioned above, any of the embodiments described in the Incorporated Patents may be used (or adapted for use)

to treat the soft palate for addressing OSA and/or snoring. Similarly, any features described in the Incorporated Patents may be incorporated into the device designs described herein.

Figure 8:
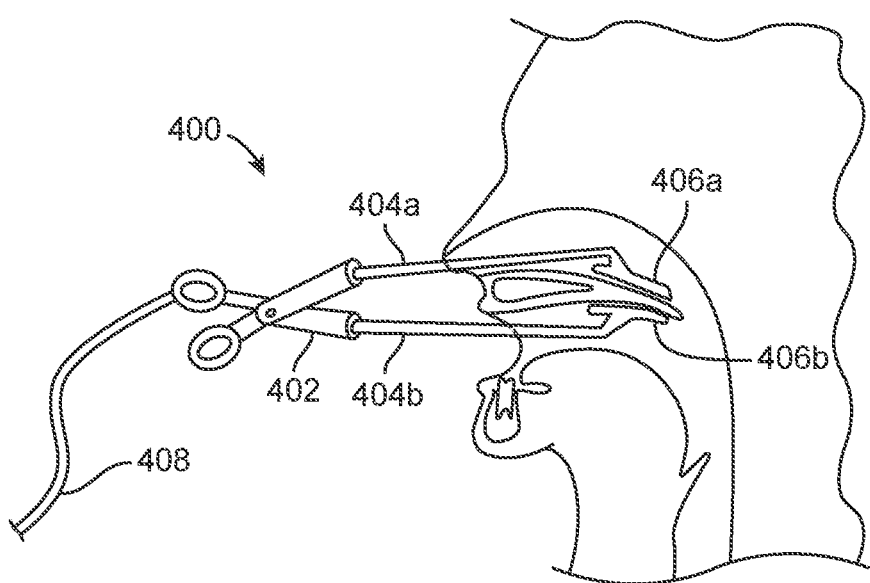
FIG. 8 is a side/cross-sectional view of a patient's head and a side view of a device being applied to the soft palate to treat OSA and/or snoring, according to another alternative embodiment.

Referring now to FIG. 8, in another alternative embodiment, a soft palate treatment device 400 may include a handle 402 that acts like a clamp or scissors handle, two shafts 404a-b extending from handle 402, two tissue treatment elements 406a-b (one at the end of each shaft 404a-b), and a power/energy cable 408. This embodiment of device 400 is similar to the clamp-type devices described in the Incorporated Patents, although it may be sized and/or shaped differently, to address the soft palate. In this embodiment, one shaft 404a is configured to extend through a nostril, so that its corresponding treatment element 406a contacts an upper surface of the soft palate, and the other shaft 404b is configured to extend through the mouth, so that its corresponding treatment element 406b contacts a lower surface of the soft palate. Treatment elements 406a-b can then be used to clamp the soft palate tissue between them and, in some embodiments, to alter the shape of the tissue. Energy may then be delivered from both treatment elements 406a-b or alternatively from one treatment element 406a or 406b, across the tissue to the other element 406b or 406a. In some embodiments, shafts 404a-b and treatment elements 406a-b may be exactly or almost exactly the same, in terms of diameter, length and shape. Alternatively, one shaft 404a-b and/or one treatment element 406a-b may be smaller, for fitting through a nostril, and the other may be larger, for fitting through the mouth.

Again, any of the features described in the Incorporated Patents may be incorporated into device 400, according to various embodiments. Although no incisions have been described above, in some embodiments, the treatment method may involve forming a small incision in the mucosa of the soft palate and advancing the treatment element through the incision to contact and treat tissue underlying the mucosa. Such embodiments are described more fully in some of the Incorporated Patents.

Figure 9:
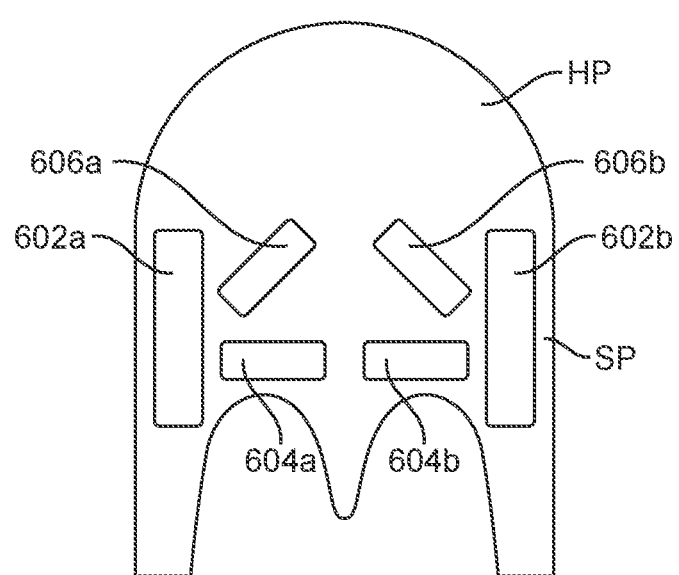
FIG. 9 is diagrammatic view looking down onto a soft palate, illustrating various locations and orientations for possible treatment of the soft palate with an energy delivery device, according to various embodiments.

FIG. 9 is diagrammatic view looking down onto a soft palate SP and hard palate HP, illustrating various locations and orientations for possible soft palate SP treatment, according to various embodiments. These are only a few examples of nearly infinite numbers of treatment locations, orientations and combinations. In any given energy delivery (or removal) treatment, using any of the embodiments described above or alternatives, therapy may be directed at any portion or portions of the soft palate SP, in any pattern, shape, size or configuration. For example, in one embodiment, treatment may be applied at or near lateral edges 602a, 602b of the soft palate SP, in a configuration of strips of tissue that are parallel to one another and in an anterior-to-posterior orientation. In another embodiment, laterally directed strips 604a, 604b near the back of the soft palate SP may be treated. In another embodiment, diagonally oriented strips 606a, 606b near the front of the soft palate SP may be treated. Alternatively, any or all of the above treatment areas may be combined in one treatment. In other embodiments, any other treatment areas, shapes, sizes and/or patterns may be used. For example, a circular treatment element may treat tissue in a circular shape. Curved treatment elements may be used in some embodiments. Treatment patterns such as X-shaped or T-shaped patterns may be used. Treatments may be overlapped in any suitable configuration. In some embodiments, treatments may be administered to shape the soft palate into a specific desired shape. For example, one part of the soft palate may be straightened, while another part may be curved. A multiple-headed treatment element may treat more than one area of tissue at a time. Again, any variation of sizes, shapes and patterns of treatment may be used, according to various alternative embodiments.

In one embodiment, during a soft palate treatment, the soft palate is tested, to see if the treatment is having a desired effect. For example, nerve stimulation may be used in some embodiments to stimulate one or more muscles of the soft palate during treatment, to observe movement of the palate. In other embodiments, air may be blown past the palate to test for vibrations or sounds emanating from the soft palate, as might happen in snoring. After testing the soft palate in one or more such ways, another area of the palate may be treated with the device (or the same area may be treated again). The palate may then be tested again. For example, another muscle of the palate may be stimulated. This process may be repeated as many times as desired, in order to treat and test the palate during the same procedure and potentially alter treatment to achieve a more desirable outcome.

Figure 10A:
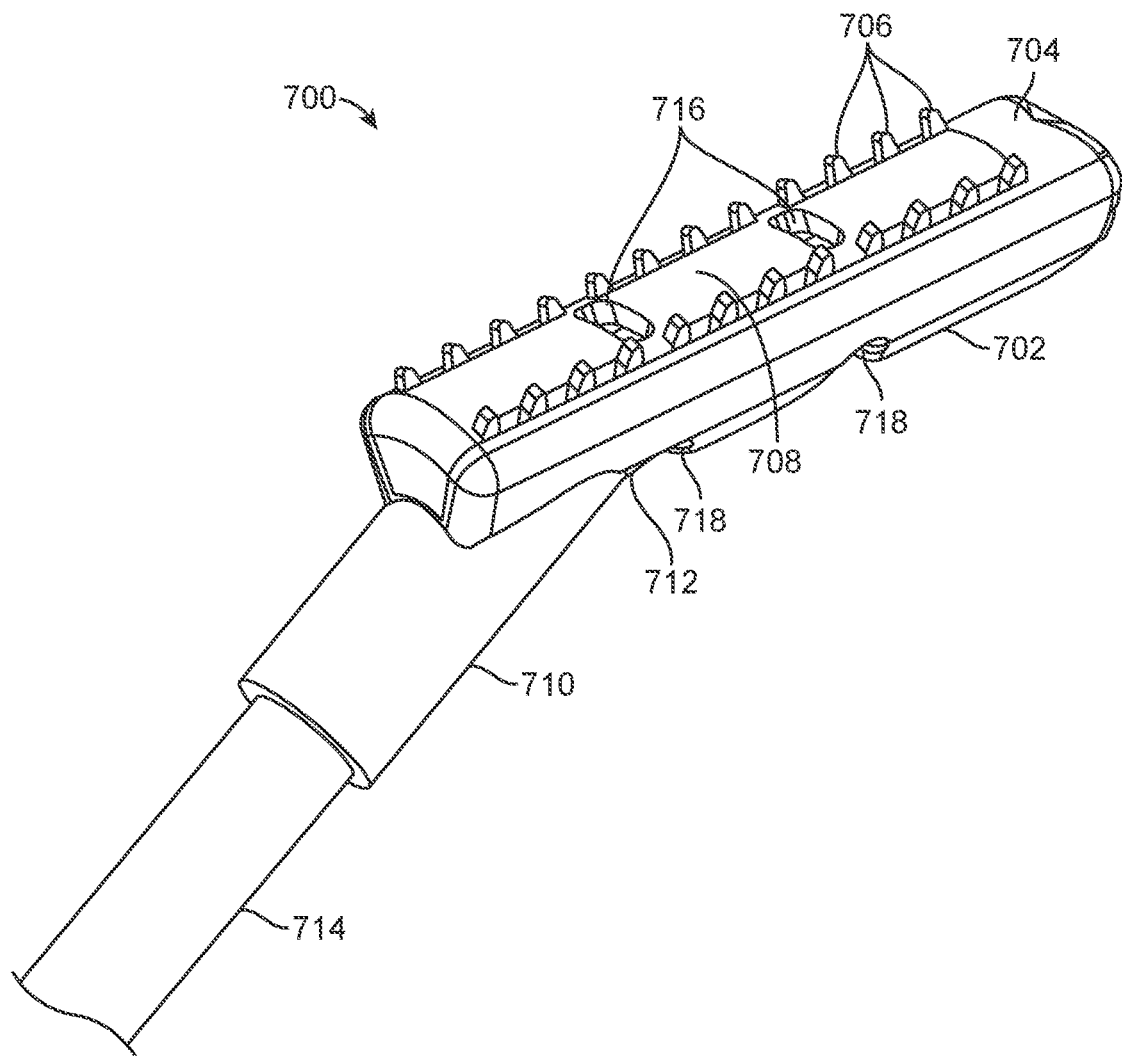
FIGS. 10A-10C are perspective, perspective and side views, respectively, of a distal portion of an energy delivery soft palate treatment device, according to one embodiment
Figure 10B:
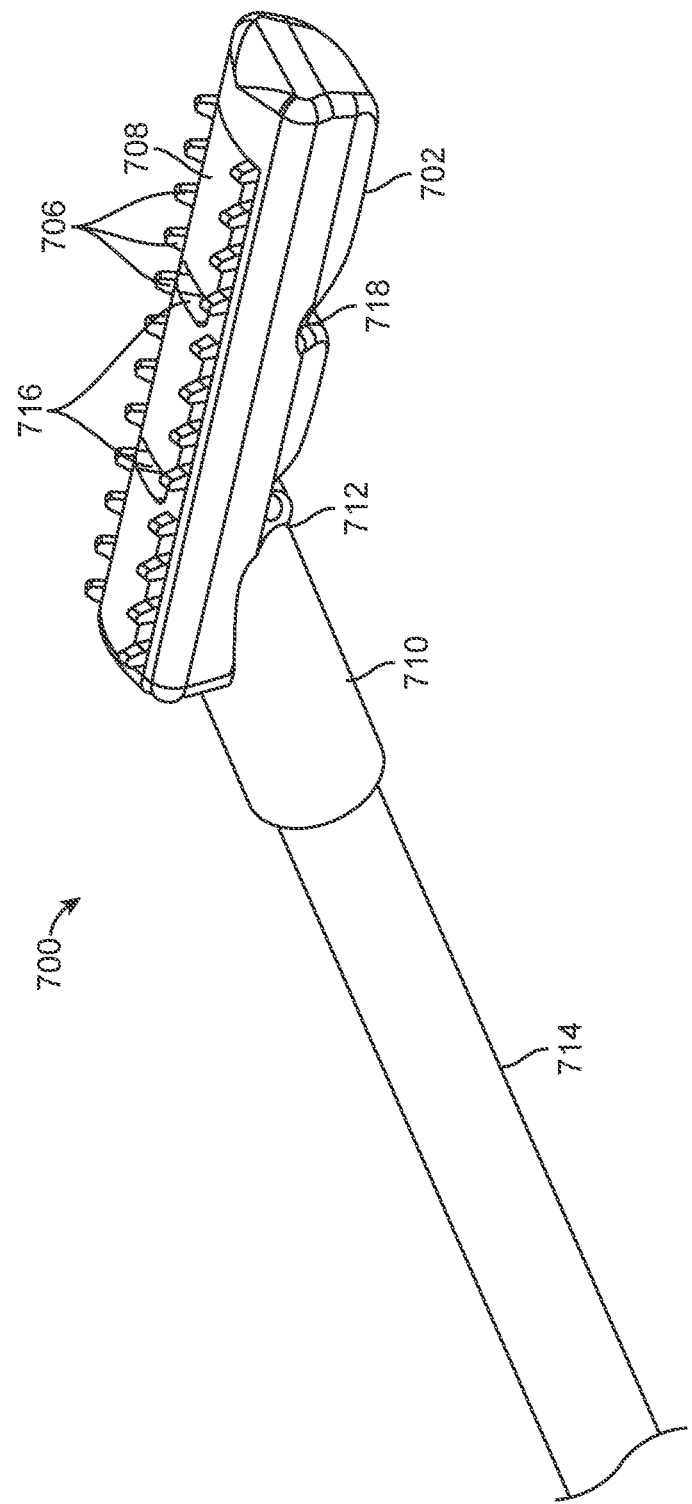
Figure 10C:
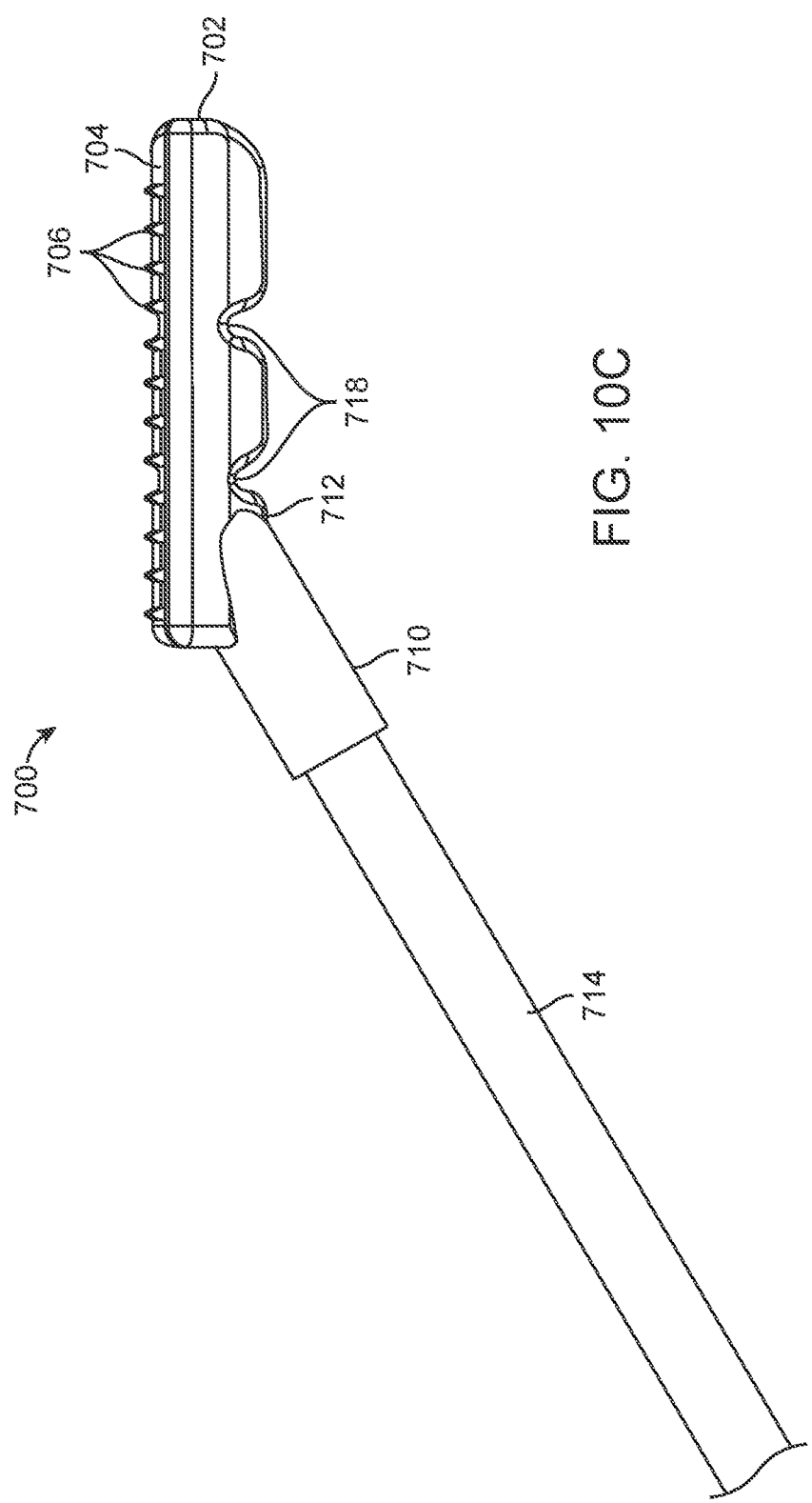

FIGS. 10A-10C are perspective views (FIGS. 10A and 10B) and a side view (FIG. 10C) of a distal portion of another embodiment of an energy delivery soft palate treatment device 700. These figures show a distal portion of a shaft 714 of the device 700, attached to a distal tip 702. The distal tip 702 includes a treatment surface 704, which includes two rows of protruding, bipolar electrodes 706 and a nonconductive material 708 positioned between the two rows of electrodes 706. Two optional apertures 716 are formed in the nonconductive material 708, which may help the distal tip 702 flex upward. The opposite (or "top") surface of the distal tip 702 may include two indents 718 (or fewer or more indents in alternative embodiments), which may allow the distal tip 702 to flex in the upper/top direction. Distal tip 702 may also include a bend 712 between the head (or distal portion) of the distal tip 702 and a neck 710 of the distal tip 702. In some embodiments, the neck 710 may fit over a distal end of the shaft 714 for manufacturing purposes.

As described previously, the distal tip 702 may have any suitable length, width, height and shape for treating a soft palate. In some embodiments, for example and as shown, the treatment surface 704 may have a slightly convex shape, with the curve of the convex surface aligned perpendicular to the longitudinal axis of the distal tip 702. In alternative embodiments, the treatment surface 704 may be flat, concave or otherwise shaped. Any suitable number, size and shape of electrodes 706 may also be used. Electrodes 706 may be protruding but not penetrating, as shown, or alternatively may be penetrating needle electrodes or flat electrodes.

In various embodiments, the distal tip 702 (or one or more portions thereof) may be rigid or flexible. A flexible or partially flexible distal tip 702, for example, may be better able to conform to the shape of the soft palate. In some embodiments, the ability of the distal tip 702 to flex may be enhanced by one or more "flex points," such as the bend 712, the apertures 716 and the indents 718. The distal tip 702 may be made of any suitable materials or combinations of rigid and/or flexible materials, such as but not limited to Nitinol, stainless steel, other metals, polymers such as urethane, silicone, low-density polyethylene (LDPE), or the like. In some embodiments, the distal tip 702 may be divided into multiple segments, for example to enhance flexibility. The apertures 716, for example, may divide the illustrated embodiment of the distal tip 702 into three segments, each having four pairs of electrodes 706. In some embodiments, each segment of electrodes 706 is separately controllable. As mentioned previously, the indents 718 on the bottom surface may also lend flexibility to the distal tip 702. Some embodiments (not shown) may also include a thermocouple or other temperature sensing device, for example on the nonconductive surface 708 between the two rows of electrodes 706, to sense temperature of the soft palate tissue being treated. The sensed temperature may be transmitted back to a control unit and used to regulate delivery of energy, based on the temperature.

In various embodiments, the apertures 716 in the treatment surface 704 may range in number from one to dozens. (The apertures 716 are also an optional feature, so some embodiments do not include any.) In addition to allowing the distal tip 702 to flex upward, the apertures 716 may serve one or more additional functions. For example, in some embodiments the apertures 716 may connect with a fluid delivery lumen running through the shaft 714 and the distal tip 702, to provide irrigation fluid at the procedure site. In addition to, or instead of, providing fluid at the procedure site, the apertures 716 may provide suction or vacuum force, for example to suction fluid out of the area or to allow the treatment surface 704 to adhere more strongly to the tissue surface being treated. In some embodiments, the apertures 716 may alternatively or additionally serve as locations for one or more temperature sensors.

To make the energy delivery device 700 easier to use, the bend 712 in the distal tip 702 may have any suitable angle. For example, some embodiments may have almost no bend 712—i.e., a straight embodiment, where the bend angle is nearly 180 degrees. Other embodiments may have a bend angle of 135 degrees or more. Or any other angle may be used, as feasible, in various embodiments. Similarly, the indents 718 may have any suitable size, shape and number, to allow the distal tip 702 to flex downward in a desired configuration to conform to the soft palate.

Referring now to FIGS. 11A-11C, another embodiment of a soft palate tissue treatment stylus 800 is illustrated. Using this embodiment or any of the embodiments described above, energy may be delivered to one or more target tissues at a predefined (or selected) tissue depth below the mucosal surface on which the treatment delivery portion of the device is placed. For example, if bipolar RF energy is the type of energy used for the treatment, the RF energy may be transmitted from one electrode or set of electrodes at or near one lateral side or edge of the treatment surface to a corresponding electrode or set of electrodes at or near an opposite lateral side or edge of the treatment surface. In traveling from one side to the other, the RF energy may pass through the mucosa and treat submucosal tissue at the selected tissue depth, in an arch-shaped or U-shaped energy delivery path. The target tissue may reside at any suitable depth, such as but not limited to a range of less than 1 mm to about 1 cm below the mucosal surface. By delivering energy to tissue below the mucosa, the treatment methods described herein may spare the mucosa from tissue trauma or damage ("mucosa sparing treatment"), which will likely improve patient satisfaction, reduce post-procedure pain and discomfort, and reduce recovery time. As mentioned above, any submucosal tissue (or combination of tissues) may be targeted in a given treatment, such as but not limited to muscle, cartilage, tendon, ligament, connective tissue, nerve, blood vessel and/or the like. Submucosal energy delivery for target tissue treatment is further described in the Incorporated References.

In some embodiments, such as the stylus 800 of FIGS. 11A-11C, in addition to providing mucosa sparing treatment by directing energy delivery to target tissue(s) below the mucosa, the stylus 800 may also include a mechanism for cooling the mucosal surface. FIG. 11A is a perspective view of a distal portion of the stylus 800, showing a shaft 802 and a treatment portion 804 (or "distal tip"), the latter including a cooling member 806 and an air vent 808. FIG. 11B is a bottom view of the same portion of the stylus 800, showing a tissue contact surface of the cooling member 806 and two longitudinal electrodes 810 disposed on opposite sides of the cooling member 806. FIG. 11C is a perspective view with the outer housing of the distal tip 804 removed to show the cooling member 806 and electrodes 810 in more detail. One electrode 810 is coupled via wiring 814 to an RF source to act as the positive electrode, and the other electrode 810 is coupled via separate wiring 816 to act as the negative electrode. The cooling member 806 delivers suction at the extreme distal end of the distal tip 804, thus sucking air into the through the cooling member 806 and into the shaft 802 (arrows). In addition to passing into the shaft 802, some air may pass through the air vent 808 on the top of the distal tip 804. The passage of air through the cooling member 806 causes convection cooling inside the cooling member 806, which in turn applies conduction cooling to the mucosa that is in contact with the cooling member 806. In various embodiments, the extreme distal end of the distal tip 804 may have one or more openings leading into the cooling member, may include a filter of the opening(s), and/or the like. The tissue contact surface of the cooling member 806 may be made of metal, plastic, polymer or any suitable material so as to convey the cooling to the mucosa without interfering with the RF energy delivery from the electrodes 810.

Referring now to FIG. 12, an alternative embodiment of a soft palate tissue treatment stylus 820 is illustrated. Here, a distal portion of the stylus 820 is shown in bottom view. The stylus 820 includes a shaft 822, a distal tip 824 (or "tissue treatment portion"), two rows of bipolar RF electrodes 830, and a cooling member 832 between the electrodes 830. This embodiment is similar to the previous embodiment, other than the configuration of the electrodes 830. In other embodiments, different types of cooling members may be used, such as but not limited to water circulating cooling members, cryogenic cooling members and the like. In various embodiments, the shaft 802 may include one or more working lumens to deliver suction (as in FIGS. 11A-12), cooling fluid, cryogenic fluid, or any other cooling agent to a cooling member. Any of the styluses described herein may include one or more cooling members, such as but not limited to those described in relation to FIGS. 11A-12.

Figure 13A:
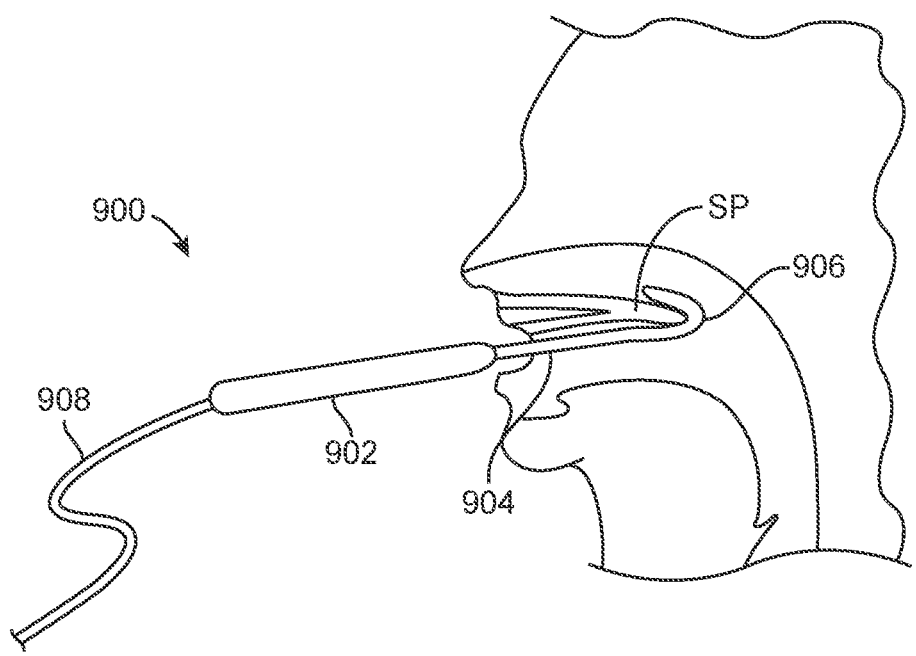
FIG. 13A is a side, cross-sectional view of a human head and a side view of a soft palate tissue treatment device, illustrating a method for using the device, according to one embodiment.
Figure 13B:
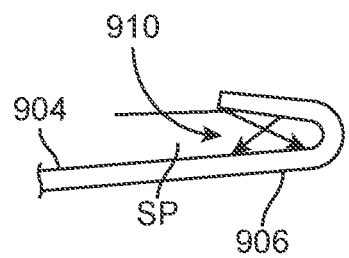
FIG. 13B is a close-up view of a distal portion of the device of FIG. 13A and the soft palate.

Referring now to FIGS. 13A and 13B, another embodiment of a soft palate tissue treatment device 900 and method are illustrated. In this embodiment, the device 900 includes a handle 902, a shaft 904, a tissue treatment portion 906 and cable 908 for connecting to a console (not shown). In this embodiment, the tissue treatment portion 906 is hook shaped or U-shaped, so that it fits around the end of the soft palate SP to contact tissue on the superior surface and the inferior surface of the soft palate SP at the same time. RF energy may be delivered from one or more electrodes on the distal portion to one or more corresponding electrodes, so that the energy travels through the soft palate SP from top to bottom, as shown in FIG. 13B, or from bottom to top. Energy may be delivered in any pattern, for example to create and X-shaped treatment pattern in one embodiment (FIG. 13B). The shaft 904 may be straight and rigid, pre-shaped with a bend and rigid, or malleable to allow the user to form it into a desired shape. In an alternative embodiment, the treatment device may be sized and shaped to be advanced through a nostril and the nasal cavity, so that the hook-shaped tissue treatment portion 906 hooks around the soft palate SP from top to bottom.

Figure 14:
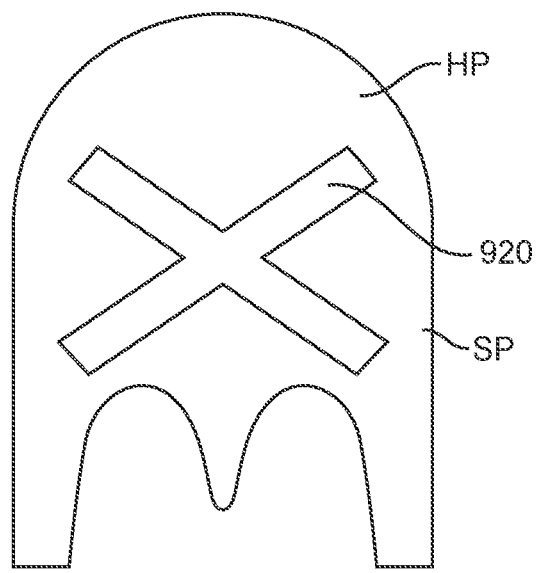
FIG. 14 is a diagrammatic view of a soft palate, illustrating a tissue treatment patter, according to one embodiment.

FIG. 14 illustrates one example of an X-shaped treatment pattern that might be achieved with the tissue treatment device 900 of FIGS. 13A and 13B. This pattern may also be achieved using at least some if not all of the other embodiments described herein.

Although various embodiments are described herein, the present invention extends beyond the specifically disclosed embodiments to other alternative embodiments and/or uses of the invention and modifications and equivalents thereof. Thus, the scope of the present invention should not be limited by the disclosed embodiments, but should be determined only by a fair reading of the claims that follow.

What is claimed is:

1. A device for treating a soft palate in a patient, the device comprising: a handle; a shaft having a proximal end attached to the handle and a distal end; an elongate treatment element extending from a distal end of the handle, the elongate treatment element comprising: a treatment surface and a back surface opposite the treatment surface; at least two energy delivery members on the treatment surface; a plurality of apertures formed in the treatment surface; and a plurality of indents formed in the back surface of the treatment element, each indent of the plurality of indents being formed opposite each aperture of the plurality of apertures; and a connector for connecting the handle with a power source, wherein the plurality of apertures are configured to provide one or more of suction for suctioning fluid away from mucosal tissue or irrigation for circulating irrigation fluid to mucosal tissue, and wherein the plurality of apertures and the plurality of indents are configured to cooperate to provide flexibility to the elongate treatment element.

2. The device of claim 1, wherein the distal end of the shaft comprises a neck that is angled relative to a longitudinal axis of the shaft, and wherein the elongate treatment element is attached to the neck.

3. The device of claim 1, wherein the at least two energy delivery members comprise two elongate bipolar radiofrequency electrodes.

4. The device of claim 1, wherein the at least two energy delivery members comprise two parallel rows of multiple bipolar radiofrequency electrodes.

5. The device of claim 4, wherein each of the radiofrequency electrodes comprises a protruding, non-penetrating electrode.

6. The device of claim 1, wherein the treatment surface has a convex shape for creating a concave deformity in the soft palate.

7. The device of claim 1, wherein the plurality of apertures is configured to provide locations for one or more temperature sensors.

8. The device of claim 1, wherein the irrigation fluid provided to mucosal tissue is a cooling fluid.

9. The device of claim 1, wherein the elongate treatment element has a hook shape, and wherein the treatment surface is configured to contact a superior surface and an inferior surface of the soft palate.

10. The device of claim 1, wherein the shaft is malleable.

11. The device of claim 1, further comprising a temperature sensing member on the elongate treatment element, for sensing a temperature of mucosal tissue in contact with the treatment surface.

12. A device for treating a soft palate in a patient, the device comprising: a handle; a shaft having a proximal end attached to the handle and a distal end; an elongate treatment element extending from a distal end of the handle, the elongate treatment element comprising: a treatment surface and a back surface opposite the treatment surface; at least two energy delivery members on the treatment surface; a first plurality of flex members formed in the treatment surface of the treatment element and a second plurality of flex members formed in the back surface of the treatment element, the first plurality of flex members and the second plurality of flex members configured to traverse a width of the treatment element; and a connector for connecting the handle with a power source, wherein the first plurality of flex members comprising apertures and the second plurality of flex members comprising indents, such that an aperture of the first plurality of flex members is positioned opposite an indent of the second plurality of flex members, wherein the apertures are configured to provide one or more of suction for suctioning fluid away from mucosal tissue or irrigation for circulating irrigation fluid to mucosal tissue, and wherein the first plurality of flex members and the second plurality of flex members are configured to cooperate to allow the elongate treatment element to flex with a curvature of the soft palate.

13. The device of claim 12, wherein the first plurality of flex members are configured to be formed perpendicular to a longitudinal axis of the treatment surface of the treatment element.

14. The device of claim 13, wherein the second plurality of flex members are configured to be formed perpendicular to a longitudinal axis of the back surface of the treatment element.

* * * * *